US012702734B2

(12) United States Patent
Rovatti et al.

(10) Patent No.: US 12,702,734 B2
(45) Date of Patent: Aug. 11, 2026

(54) APPARATUS FOR EXTRACORPOREAL BLOOD TREATMENT

(71) Applicant: GAMBRO LUNDIA AB, Lund (SE)

(72) Inventors: Paolo Rovatti, Finale Emilia (IT); Alessandro Surace, Carpi (IT)

(73) Assignee: Gambro Lundia AB, Lund (SE)

(*) Notice: Subject to any disclaimer, the term of this patent is extended or adjusted under 35 U.S.C. 154(b) by 418 days.

(21) Appl. No.: 18/277,640

(22) PCT Filed: Feb. 10, 2022

(86) PCT No.: PCT/EP2022/053227

§ 371 (c)(1),
(2) Date: Aug. 17, 2023

(87) PCT Pub. No.: WO2022/175154

PCT Pub. Date: Aug. 25, 2022

(65) Prior Publication Data

US 2024/0123127 A1 Apr. 18, 2024

(30) Foreign Application Priority Data

Feb. 18, 2021 (EP) .................................... 21157807

(51) Int. Cl.
*A61M 1/16* (2006.01)

(52) U.S. Cl.
CPC ........ *A61M 1/1613* (2014.02); *A61M 1/1607* (2014.02); *A61M 1/1611* (2014.02);
(Continued)

(58) Field of Classification Search
CPC ................. A61M 1/16–1619; G16H 20/00–90
See application file for complete search history.

(56) References Cited

U.S. PATENT DOCUMENTS

| | | | | |
|---|---|---|---|---|
| 5,938,938 A * | 8/1999 | Bosetto | .................. | A61M 1/16 210/647 |
| 8,608,658 B2 | 12/2013 | Brugger | | |

(Continued)

FOREIGN PATENT DOCUMENTS

| | | |
|---|---|---|
| EP | 1810703 | 10/2009 |
| EP | 2890289 | 4/2018 |

(Continued)

OTHER PUBLICATIONS

PCT Search Report and Written Opinion for PCT/EP2022/053227 dated May 4, 2022 (13 pages).

(Continued)

*Primary Examiner* — Leslie R Deak
*Assistant Examiner* — Linnae E. Raymond
(74) *Attorney, Agent, or Firm* — Mueting Raasch Group

(57) ABSTRACT

A control unit of an apparatus for extracorporeal blood treatment is configured to perform a control procedure comprising: calculating parameter control values to be set during a time interval after the instant in which the control is made, on the basis of actual values and of prescription values of variation in blood volume, ultrafiltration flow rate, concentration of sodium and/or potassium and heart rate or variation of heart rate of the patient; imposing the parameter control values during the time interval consecutive to the instant in which the control is made such that the actual values of the variation in blood volume track the prescription values of the variation in blood volume over a predetermined treatment time and the actual values of the heart rate or variation of heart rate track the prescription values of the heart rate or variation of heart rate over the predetermined treatment time.

30 Claims, 10 Drawing Sheets

(52) U.S. Cl.
CPC ............... *A61M 2205/3303* (2013.01); *A61M 2205/3334* (2013.01); *A61M 2230/005* (2013.01); *A61M 2230/04* (2013.01); *A61M 2230/20* (2013.01)

(56) References Cited

U.S. PATENT DOCUMENTS

| | | | | |
|---|---|---|---|---|
| 9,320,842 | B2 * | 4/2016 | Orhan | A61M 1/287 |
| 9,486,568 | B2 | 11/2016 | Wagner | |
| 10,342,910 | B2 | 7/2019 | Strohhoefer | |
| 2014/0323942 | A1 | 10/2014 | Atallah | |
| 2017/0281849 | A1 | 10/2017 | Toyoda | |

FOREIGN PATENT DOCUMENTS

| | | | | |
|---|---|---|---|---|
| EP | 2874540 | | 9/2018 | |
| EP | 3545985 | | 10/2019 | |
| WO | WO-2011080190 | A1 * | 7/2011 | A61B 5/0215 |
| WO | WO 2012/172398 | | 12/2012 | |
| WO | WO-2012172398 | A1 * | 12/2012 | A61M 1/1605 |
| WO | WO 2015/081221 | | 6/2015 | |
| WO | WO-2015081221 | A1 * | 6/2015 | G16H 40/67 |
| WO | WO 2016/126648 | | 8/2016 | |
| WO | WO 2018/045102 | | 3/2018 | |

OTHER PUBLICATIONS

Extended European Search Report for Application No. 21157807.5 dated Aug. 11, 2021 (8 pages).

* cited by examiner

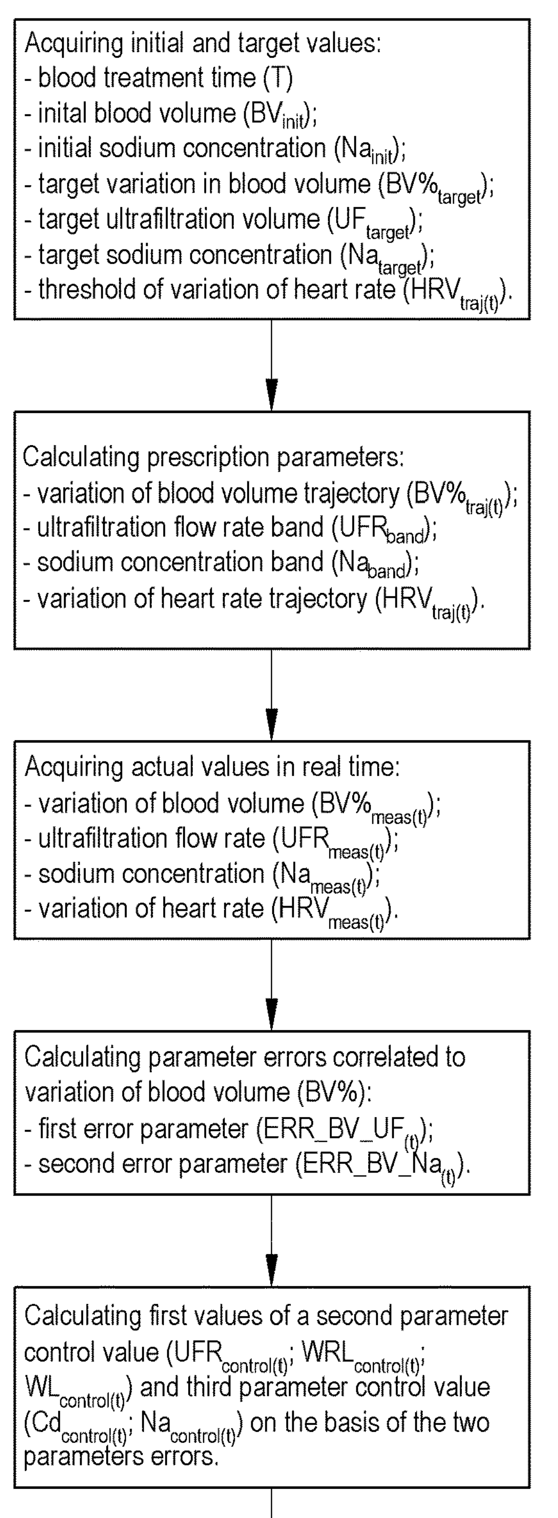

Comparing the measured value of the variation fo heart rate ($HRV_{meas(t)}$) with the prescription value of the variation of heart rate ($HRV_{traj(t)}$).

Correcting the first values of the second parameter control value ($UFR_{control(t)}$; $WRL_{control(t)}$; $WL_{control(t)}$) and of the third parameter control value ($Cd_{control(t)}$; $Na_{control(t)}$) as a function of the previous comparison.

Imposing the corrected second parameter control value ($UFR_{control(t)}$; $WLR_{control(t)}$; $WL_{control(t)}$) and the corrected third parameter control value ($Cd_{control(t)}$; $Na_{control(t)}$) such that the actual values of the variation of blood volume ($BV\%_{meas(t)}$) track the prescription values of the variation of blood volume ($BV\%_{traj(t)}$) over the predetermined treatment time (T); and the actual values of the variation of heart rate ($HRV_{meas(t)}$) track the prescription values of the variation of heart rate ($HRV_{traj(t)}$) over the predetermined treatment time (T).

FIG.2A

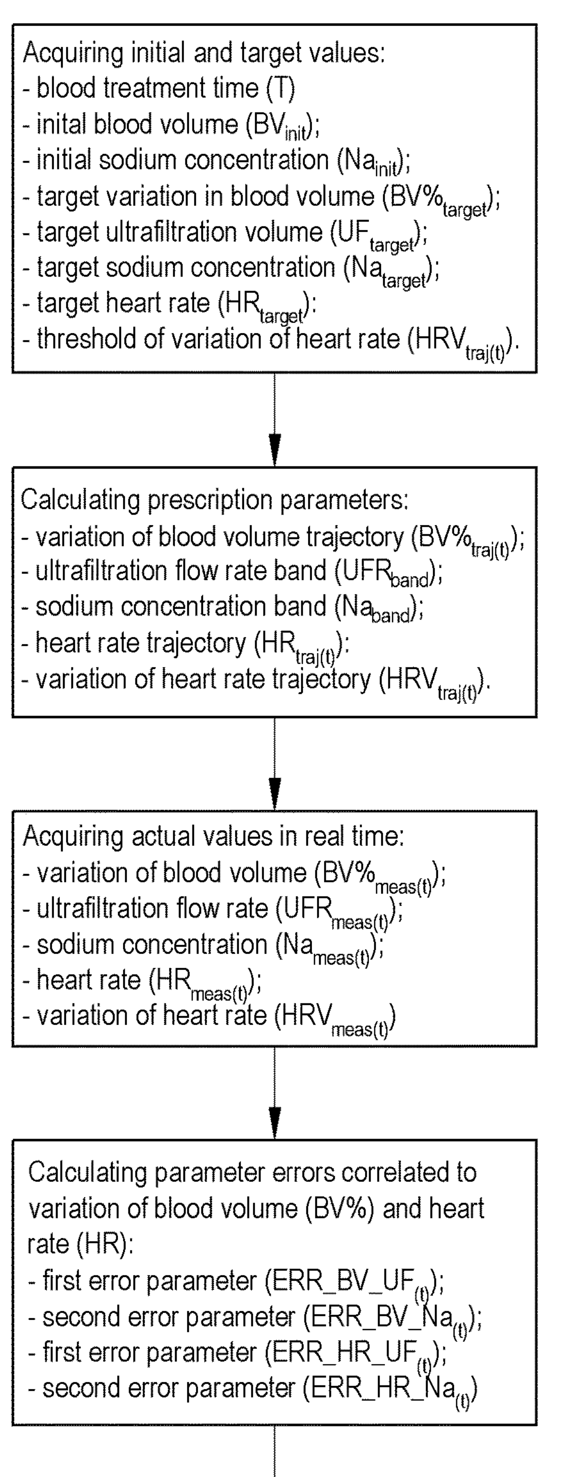

Calculating first values of a second parameter control value ($UFR_{control(t)}$; $WRL_{control(t)}$; $WL_{control(t)}$) and of a third parameter control value ($Cd_{control(t)}$; $Na_{control(t)}$) on the basis of the four parameter errors.

Comparing the measured value of the variation fo heart rate ($HRV_{meas(t)}$) with the prescription value of the variation of heart rate ($HRV_{traj(t)}$).

Correcting the first values of the second parameter control value ($UFR_{control(t)}$; $WRL_{control(t)}$; $WL_{control(t)}$) and of the third parameter control value ($Cd_{control(t)}$; $Na_{control(t)}$) as a function of the previous comparison.

Imposing the corrected second parameter control value ($UFR_{control(t)}$; $WLR_{control(t)}$; $WL_{control(t)}$) and the corrected third parameter control value ($Cd_{control(t)}$; $Na_{control(t)}$) such that the actual values of the variation of blood volume ($BV\%_{meas(t)}$) track the prescription values of the variation of blood parameter ($BV\%_{traj(t)}$) over the predetermined treatment time (T); and the actual values of the heart rate and variation of heart rate ($HR_{meas(t)}$; $HRV_{meas(t)}$) track the prescription values of the heart rate and variation of heart rate ($HR_{traj(t)}$; $HRV_{traj(t)}$) over the predetermined treatment time (T).

FIG.5A

APPARATUS FOR EXTRACORPOREAL BLOOD TREATMENT

This application is a U.S. National Stage Application of International Application No. PCT/EP2022/053227 filed Feb. 10, 2022, which was published in English on Aug. 25, 2022, as International Publication No. WO 2022/175154 A1. International Application No. PCT/EP2022/053227 claims priority to European Application No. 21157807.5 filed Feb. 18, 2021.

The present invention relates to an apparatus for extracorporeal blood treatment.

An apparatus for extracorporeal blood treatment comprises at least one treatment unit (for example a dialyser or a filter or ultrafilter or a plasma filter or a filtering unit of another type) having a semipermeable membrane which separates the treatment unit into two chambers. An extracorporeal blood circuit enables circulation of blood removed from a patient internally of the first chamber. At the same time and typically in a counter-current direction with respect to the blood, a treatment fluid is made to circulate through an appropriate circuit in the second chamber of the treatment unit. This type of apparatus for blood treatment, known as dialysis apparatus, may be used for removal of excess solutes and fluids from the blood of patients suffering from kidney failure. A particular type of apparatus for blood treatment, known as hemofiltration or hemodiafiltration apparatus, further comprises one or more infusion lines predisposed to send a replacement fluid into the extracorporeal blood circuit. The infusion line or lines are connected upstream and/or downstream with respect to the treatment unit. The above-described blood treatment apparatus may be controlled in various ways during patient treatment.

Document WO 2012/172398 A1 discloses an apparatus for extracorporeal blood treatment comprising sensors for determining a first parameter relating to a patient's blood volume, a second parameter relating to an ultrafiltration flow rate or to a patient's weight loss rate, a third parameter relating to a conductivity or concentration of a liquid crossing the dialysis line and/or the infusion line and a fourth parameter relating to an infusion flow rate. The apparatus comprises a control unit for performing a control procedure comprising: receiving, from the sensors, the measured values of the above-cited parameters and calculating, on the basis of the measured values and the prescription values of the variation in blood volume, the weight loss, the plasma conductivity or sodium concentration, the infusion volume, control values to be imposed during a time interval following the control instant.

WO 2012/172398 A1 allows to reach the desired objectives of weight loss and plasma sodium concentration in the patient without causing problems of hypovolemia. WO 2012/172398 A1 is also able to operate in the presence of high convective exchange and to guarantee at the same time a high degree of patient comfort and therefore to improve quality of life of patients.

The Applicant observed that dialysis induced hypovolemia (IDH) caused by ultrafiltration and by osmolality reduction may be prevented through compensation of sudden variations in the relative Blood Volume Change (BV %), as allowed by WO 2012/172398 A1. The Applicant further noted that dialysis induced hypovolemia (IDH) caused by ultrafiltration and by osmolality reduction is not the only cause of dialysis induced hypotension occurrences. Indeed, another frequent cause of IDH is linked to the incorrect cardiac function during the treatment (e.g.: autonomic dysfunction or decreased cardiac reserve). Also known are technical solutions, for example described in document U.S. Pat. No. 10,342,910 B2, able to predict intradialytic parameters for correction or reduction of intradialytic hypotensive situations, in which blood pressure is monitored to control UF rate and blood volume and heart beat may be used as input parameter in addition to blood pressure. The prognosis parameters may be evaluated compared to threshold values and/or may be displayed.

Document U.S. Pat. No. 9,486,568 B2 discloses a control loop to monitor patient condition during dialysis treatment, in particular to recognize hypotensive episodes. The monitored parameters comprise relative blood volume, blood pressure and may comprise heart rate or course of heart rate. The monitored parameters are used to calculate a corresponding UF rate.

SUMMARY

An aim of the present invention is to make available an apparatus for blood treatment which is able to reduce and/or prevent hypotension occurrences in patients under treatment.

An aim of the present invention is to reduce and/or prevent hypotension occurrences due to ultrafiltration and by osmolality reduction and/or to cardiac dysfunctions shown during the HD treatments. In particular, aim of the present invention is to prevent/reduce IDH episodes also in patients showing a good intravascular refilling rate but having IDH for cardiac dysfunctions.

A further aim of the present invention is to make available an apparatus which is able to continuously modulate UF (or weight loss) and/or sodium and/or potassium concentration or any other substance typically composing the dialysis fluid (e.g. bicarbonate, calcium, magnesium, etc.), in order to get the best possible compromise between reaching the prescription targets and reducing and/or preventing the cited hypotension occurrences of the patient, thus improving the comfort of the patient during treatment.

A further aim of the invention is to provide an apparatus which, though accelerating the search sequence for the wanted trajectories of prescription parameters, is however able to operate safely.

At least one of the above-indicated aims is substantially attained by an apparatus for blood treatment as in one or more of the appended claims. Some aspects of the invention are now described.

In a $1^{st}$ aspect, an apparatus for extracorporeal blood treatment comprises:

- a treatment unit having a first chamber and a second chamber separated from one another by a semipermeable membrane;
- a blood removal line connected to an inlet port of the first chamber and predisposed to remove blood from a patient,
- a blood return line connected to an outlet port of the first chamber and predisposed to return treated blood to the patient; the blood removal line, the blood return line and the first chamber being part of an extracorporeal blood circuit;
- at least a fluid evacuation line connected to an outlet port of the second chamber;
- a supply line connected to an inlet port of the second chamber and/or connected to the extracorporeal blood circuit;
- sensor devices for detecting actual values of parameters of the extracorporeal blood treatment;

a control unit connected with the sensor devices and configured to receive prescription values of said parameters to be reached in the patient or to follow over a predetermined treatment time and to obtain, through the sensor devices, the actual values of said parameters during the extracorporeal blood treatment; wherein said parameters comprises:

a first parameter relating to a variation in blood volume of the patient;

a second parameter relating to an ultrafiltration flow rate through the semipermeable membrane or to a weight loss rate of the patient or to an accumulated weight loss;

a third parameter relating to a conductivity of a liquid crossing the supply line or to a concentration of a substance in a liquid crossing the supply line, optionally sodium and/or potassium or any other substance typically composing the liquid crossing the supply line (e.g. bicarbonate, calcium, magnesium, etc.);

at least a fourth parameter relating to heart rate of the patient;

wherein the control unit is configured to perform, at temporally consecutive control instants, a control procedure comprising:

calculating, on the basis of the actual values and of the prescription values, the following control values to be set during a time interval after the instant in which the control is made:

a second parameter control value; and/or a third parameter control value;

imposing at least one of the second parameter control value and third parameter control value during the time interval consecutive to the instant in which the control is made such that:

the actual values of the first parameter track the prescription values of the first parameter over the predetermined treatment time; and the actual values of the fourth parameter track the prescription values of the fourth parameter over the predetermined treatment time.

In a 2nd aspect, a method for reducing and/or preventing hypotension occurrences in patients undergoing extracorporeal blood treatment, comprises:

setting prescription values of parameters to be reached in a patient or to follow over a predetermined treatment time;

detecting actual values of said parameters during the extracorporeal blood treatment;

wherein said parameters comprises:

a first parameter relating to a variation in blood volume of the patient;

a second parameter relating to an ultrafiltration flow rate through a semipermeable membrane or to a weight loss rate of the patient or to an accumulated weight loss;

a third parameter relating to a conductivity of a liquid crossing a supply line or to a concentration of a substance in a liquid crossing the supply line, optionally sodium and/or potassium or any other substance typically composing the liquid crossing the supply line (e.g. bicarbonate, calcium, magnesium, etc.);

at least a fourth parameter relating to heart rate of the patient;

performing, at temporally consecutive control instants, the following control steps:

calculating, on the basis of the actual values and of the prescription values, the following control values to be set during a time interval after the instant in which the control is made:

a second parameter control value; and/or a third parameter control value;

imposing at least one of the second parameter control value and third parameter control value during the time interval consecutive to the instant in which the control is made such that:

the actual values of the first parameter track the prescription values of the first parameter over the predetermined treatment time; and the actual values of the fourth parameter track the prescription values of the fourth parameter over the predetermined treatment time.

In a 3rd aspect, the method of aspect 2 is achieved through the apparatus of aspect 1 and/or of one or more of the following aspects.

In a 4th aspect in accordance with any of the previous aspects 1 to 3, the fourth parameter is acquired continuously and in real time; optionally the fourth parameter is the heart rate (HR); optionally the actual value of the heart rate is an average of heart rate (HR) over a time interval, optionally the time interval is few seconds, optionally 5 s to 30 s.

In a 5th aspect in accordance with any of the previous aspects 1 to 3, the fourth parameter is variation of heart rate, wherein the variation of heart rate is calculated in real time from an heart signal; optionally the actual value of variation of heart rate is calculated at each heartbeat or is an average over a plurality of heartbeats, optionally a number of heartbeats of said plurality is between 5 and 10. Variation of heart rate or heart rate variability (HRV) is the physiological phenomenon of the variation in the time interval between consecutive heartbeats.

In a 6th aspect in accordance with the previous aspect 5, the heart rate is acquired continuously and in real time and/or the variation of heart rate is calculated from the heart rate; optionally, a heart signal is acquired continuously and in real time, wherein the heart rate is computed by using the heart signal acquired and/or the variation of heart rate is computed by using the heart signal acquired.

In a 7th aspect in accordance with any of the previous aspects 5 or 6, the variation of heart rate is calculated through: time domain methods or geometric methods or frequency-domain methods or non-linear methods.

In a 7th bis aspect, the actual values of the fourth parameter, optionally of the heart rate and/or of the variation of heart rate, is/are displayed on a display.

In a 8th aspect in accordance with any of the previous aspects, the prescription values of the fourth parameter define a fourth parameter trajectory and tracking the prescription values of the fourth parameter comprises: keeping or moving the actual values of the fourth parameter on said fourth parameter trajectory or in a neighbourhood of said fourth parameter trajectory.

In a 9th aspect in accordance with the previous aspect 8, the fourth parameter trajectory comprises a succession of points defining a line over treatment time; optionally the fourth parameter trajectory is constant or time-varying; optionally, the fourth parameter trajectory is constant over the treatment time or decreases or increases over the treatment time; optionally, the fourth parameter trajectory is a straight line.

In a 10th aspect in accordance with any of the previous aspects 1 to 9, the prescription values of the fourth parameter are defined by a fourth parameter band and tracking the prescription values of the fourth parameter comprises: keeping or moving the actual values of the fourth parameter within said fourth parameter band; optionally, a fourth parameter trajectory is a mid line of the fourth parameter band.

In a $10^{th}$ bis aspect according to the previous aspect 10, the mid line of the fourth parameter band is in the middle, i.e. equally spaced from the upper trajectory and lower trajectory, or is eccentric compared to the upper trajectory and lower trajectory.

In a $11^{th}$ aspect in accordance with the previous aspect 10, the fourth parameter band comprises a plurality of points delimited between an upper trajectory and a lower trajectory over treatment time; optionally the upper trajectory is constant or time-varying; optionally, the upper trajectory is constant over the treatment time or decreases or increases over the treatment time; optionally, the upper trajectory is a straight line; optionally, the lower trajectory is constant or time-varying; optionally, the lower trajectory is constant over the treatment time or decreases or increases over the treatment time; optionally, the lower trajectory is a straight line.

In a $12^{th}$ aspect in accordance with any of the previous aspects 1 to 11, the prescription values of the fourth parameter define a fourth parameter threshold and tracking the prescription values of the fourth parameter comprises: keeping or moving the actual values of the fourth parameter below or above said fourth parameter threshold; optionally, the fourth parameter threshold is an upper trajectory or a lower trajectory of a fourth parameter band.

In a $13^{th}$ aspect in accordance with the previous aspect 12, the fourth parameter threshold comprises a succession of points defining a line over treatment time; optionally, the fourth parameter threshold is constant or time-varying; optionally, the fourth parameter threshold is constant over the treatment time or decreases or increases over the treatment time; optionally, the fourth parameter threshold is a straight line.

In a $14^{th}$ aspect in accordance with any of the previous aspects, calculating the second parameter control value comprises:

- comparing the actual value of the fourth parameter with the prescription value of the fourth parameter at the instant (t) in which the control is made;
- calculating the second parameter control value to be imposed during the time interval (Δt) consecutive to the instant (t) as a function of said comparison.

In a $15^{th}$ aspect in accordance with the previous aspect and to aspect 13, the fourth parameter is the variation of heart rate and the prescription values of the fourth parameter is the fourth parameter threshold; wherein, if the actual value of the variation of heart rate is above the fourth parameter threshold or if a plurality of consecutive actual values of heart rate are above the fourth parameter threshold, the second parameter control value, to be imposed during the time interval (Δt) consecutive to the instant (t) in which the control is made, is decreased with respect to the actual value of the second parameter at the instant (t) in which the control is made.

In a $16^{th}$ aspect in accordance with any of the previous aspects, calculating the third parameter control value comprises:

- comparing the actual value of the fourth parameter with the prescription value of the fourth parameter at the instant (t) in which the control is made;
- calculating the third parameter control value to be imposed during the time interval consecutive to the instant as a function of said comparison.

In a $17^{th}$ aspect in accordance with the previous aspect and to aspect 13, the fourth parameter is the variation of heart rate and the prescription values of the fourth parameter is the fourth parameter threshold; wherein, if the actual value of the variation of heart rate is above the fourth parameter threshold or if a plurality of consecutive actual values of heart rate are above the fourth parameter threshold, the third parameter control value, to be imposed during the time interval (Δt) consecutive to the instant (t) in which the control is made, is decreased with respect to the actual value of the third parameter at the instant (t) in which the control is made.

In a $18^{th}$ aspect in accordance with the previous aspect 8 or 9, the fourth parameter is the heart rate and the prescription values of the fourth parameter are the fourth parameter trajectory; wherein calculating the second parameter control value comprises:

- receiving the fourth parameter trajectory and the prescription values of the second parameter;
- determining at least a first error parameter correlated to the fourth parameter on the basis of:
  - a difference between the actual value of the fourth parameter at the control instant (t) and a corresponding value on the fourth parameter trajectory; and
  - a difference between an actual value of the second parameter at the control instant (t) and at least a corresponding prescription value of the second parameter;
- calculating the second parameter control value on the basis of the first error parameter, correlated to the fourth parameter, and of the actual value of the second parameter relating to a preceding control instant.

In a $18^{th}$ bis aspect in accordance with the previous aspect 18, calculating the second parameter control value further comprises:

- determining at least a first error parameter correlated to the first parameter on the basis of:
  - a difference between the actual value of the first parameter at the control instant (t) and a corresponding value on the first parameter trajectory; and
  - a difference between an actual value of the second parameter at the control instant (t) and at least a corresponding prescription value of the second parameter;
  - calculating the second parameter control value on the basis of the first error parameter correlated to the fourth parameter, of the first error parameter correlated to the first parameter and of the actual value of the second parameter relating to a preceding control instant.

In a $19^{th}$ aspect in accordance with the previous aspect 8 or 9 or 18 or 18 bis, the fourth parameter is the heart rate and the prescription values of the fourth parameter are the fourth parameter trajectory;

- wherein calculating the third parameter control value comprises:
  - receiving the fourth parameter trajectory and the prescription values of the third parameter;
  - determining at least a second error parameter correlated to the fourth parameter on the basis of:
    - a difference between the actual value of the fourth parameter at the control instant (t) and a corresponding value on the fourth parameter trajectory; and a difference between an actual value of the third parameter at the control instant (t) and at least a corresponding prescription value of the third parameter;

calculating the third parameter control value on the basis of the second error parameter, correlated to the fourth parameter, and of the actual value of the third parameter relating to a preceding control instant.

In a $19^{th}$ bis aspect in accordance with the previous aspect 19, calculating the third parameter control value further comprises:

determining at least a second error parameter correlated to the first parameter on the basis of:

a difference between the actual value of the first parameter at the control instant (t) and a corresponding value on the first parameter trajectory; and a difference between an actual value of the third parameter at the control instant (t) and at least a corresponding prescription value of the third parameter;

calculating the third parameter control value on the basis of the second error parameter correlated to the fourth parameter, of the second error parameter correlated to the first parameter and of the actual value of the third parameter relating to a preceding control instant.

In a $20^{th}$ aspect in accordance with any of the previous aspects, the prescription values of the second parameter define a second parameter band delimited between an upper trajectory and a lower trajectory over treatment time; optionally, the upper trajectory of the second parameter band decreases over treatment time; optionally, the lower trajectory of the second parameter band is constant or decreases over treatment time; optionally, the upper and/or lower trajectory/ies is/are straight line/s; optionally, the upper and lower trajectories converge one towards the other over treatment time.

In a $21^{st}$ aspect in accordance with the previous aspect 20, the calculated second parameter control values are less than or equal to the upper trajectory of the second parameter band and greater than or equal to the lower trajectory of the second parameter band.

In a $22^{nd}$ aspect in accordance with any of the previous aspects, the prescription values of the third parameter define a third parameter band delimited between an upper trajectory and a lower trajectory over treatment time; optionally, the upper trajectory of the third parameter band decreases over treatment time; optionally, the lower trajectory of the third parameter band is constant or decreases over treatment time; optionally, the upper and/or lower trajectory/ies is/are straight line/s; optionally, the upper and lower trajectories converge one towards the other over treatment time.

In a $23^{rd}$ in accordance with the previous aspect 22, the calculated third parameter control values are less than or equal to the upper trajectory of the third parameter band and greater than or equal to the lower trajectory of the third parameter band.

In a $24^{th}$ aspect in accordance with any of the previous aspects, first values of the second parameter control value and/or of the third parameter control value are calculated on the basis of the actual values and of the prescription values of the first parameter, second parameter and third parameter and then said first values of the second parameter control value and/or of the third parameter control value are corrected and/or limited on the basis of the actual values and of the prescription values of the fourth parameter.

In a $24^{th}$ bis aspect in accordance with any of the previous aspects, the at least a fourth parameter comprises both heart rate and variation of heart rate; wherein first values of the second parameter control value and/or of the third parameter control value are calculated on the basis of the actual values and of the prescription values of the first parameter, second parameter, third parameter and heart rate and then said first values of the second parameter control value and/or of the third parameter control value are corrected and/or limited on the basis of the actual values and of the prescription values of the variation of heart rate.

In a $25^{th}$ aspect in accordance with any of the previous aspects, first, only the third parameter control value is imposed to track the prescription values of the first parameter and/or of the fourth parameter and, then, the second parameter control value is also imposed if the prescription values of the first parameter and/or of the fourth parameter is/are not tracked correctly.

In a $26^{th}$ aspect in accordance with any of the previous aspects, the prescription values of the first parameter define a first parameter trajectory and tracking the prescription values of the first parameter comprises: keeping or moving the actual values of the first parameter on said first parameter trajectory or in a neighbourhood of said first parameter trajectory; optionally the first parameter trajectory decreases over treatment time.

In a $27^{th}$ aspect in accordance with any of the previous aspects, the prescription values of the first parameter define a first parameter band delimited between an upper trajectory and a lower trajectory over treatment time and tracking the prescription values of the first parameter comprises: keeping or moving the actual values of the first parameter in said first parameter band; optionally the upper trajectory and the lower trajectory decrease over treatment time; optionally, a mid-line of the first parameter band defines a first parameter trajectory.

In a $27^{th}$ bis aspect according to the previous aspect 27, the mid line of the first parameter band is in the middle, i.e. equally spaced from the upper trajectory and lower trajectory, or is eccentric compared to the upper trajectory and lower trajectory.

In a $28^{th}$ aspect in accordance with the previous aspect 27, the control procedure or the method comprises: issuing an alarm signal and/or stopping the blood treatment if the actual values of the first parameter are out of the first parameter band, optionally for a given time.

In a $29^{th}$ aspect in accordance with any of the previous aspects 10 to 13, the control procedure or the method comprises: issuing an alarm signal and/or stopping the blood treatment if the actual values of the fourth parameter are out of the fourth parameter band, optionally for a given time.

In a $30^{th}$ aspect in accordance with any of the previous aspects, the sensor devices comprise: at least a first sensor active on the extracorporeal blood circuit for detecting the actual values of the first parameter.

In a $31^{st}$ aspect in accordance with any of the previous aspects, the sensor devices comprise: at least a second sensor active at least on the fluid evacuation line for determining the actual values of the second parameter; optionally, a flow sensor is active on the evacuation line and a flow sensor on the supply line such as to provide the control unit CPU with the instant value of the respective flows and thus enable the control unit CPU to calculate an instant ultrafiltration flow.

In a $32^{nd}$ aspect in accordance with any of the previous aspects, the sensor devices comprise: at least a third sensor active on the supply line for determining the actual values of the third parameter.

In a $33^{rd}$ aspect in accordance with any of the previous aspects, the sensor devices comprise: a fourth sensor active on the patient and/or on the extracorporeal blood circuit (on the blood removal line and/or on the blood return line) for determining the actual values of the fourth parameter.

In a 34$^{th}$ aspect in accordance with the previous aspect 32, the fourth sensor is not intrusive and/or wearable and/or portable; optionally, the fourth sensor is selected from the group comprising: a patch, a wristband or an armband, a chest strap, a wearable electrode based ECG, a touch device, a breathable heart rate monitor, a contactless sensor, an ingestible pill.

In a 35$^{th}$ aspect in accordance with any of the previous aspects, the apparatus comprises: a first regulating device for regulating the second parameter, the first regulating device being connected to the control unit and being active on at least one of the extracorporeal blood circuit and the fluid evacuation line.

In a 36$^{th}$ aspect in accordance with the previous aspect 35, the step of imposing the control values during the procedure comprises: commanding the first regulating device to impose the second parameter control value.

In a 37$^{th}$ aspect in accordance with any of the previous aspects, the apparatus comprises: a second regulating device for regulating a composition of the dialysis liquid, the second regulating device being connected to the control unit and being active on the supply line for regulating the third parameter.

In a 38$^{th}$ aspect in accordance with previous aspect 37, the step of imposing the control values during the procedure comprises: commanding the second regulating device to impose the third parameter control value.

In a 39$^{th}$ aspect in accordance with any of the previous aspects, the actual values of the first parameter are obtained measuring concentration of haemoglobin in the blood and calculating the variation in blood volume from the measured concentration of haemoglobin.

In a 40$^{th}$ aspect in accordance with the previous aspect 39 together with aspect 26 or 27, receiving or setting the prescription values of the first parameter comprises:

- estimating or measuring an initial concentration of haemoglobin and/or an initial blood volume;
- setting a target variation in blood volume to be reached at the end of the blood treatment; setting a blood treatment time;
- calculating the first parameter trajectory taking into account the initial concentration of haemoglobin and/or initial blood volume, the target variation in blood volume and the blood treatment time.

In a 41$^{st}$ aspect in accordance with the previous aspect 20 or 21, receiving or setting the prescription values of the second parameter comprises:

- setting a target ultrafiltration volume or target weight loss to be reached at the end of the blood treatment;
- setting a blood treatment time;
- calculating the second parameter band taking into account the target ultrafiltration volume or target weight loss and the treatment time.

In a 42$^{nd}$ aspect in accordance with the previous aspect 22 or 23, receiving or setting the prescription values of the third parameter comprises:

- estimating or measuring an initial conductivity or an initial concentration of the substance, optionally sodium and/or potassium or any other substance typically composing the liquid crossing the supply line (e.g. bicarbonate, calcium, magnesium, etc.);
- setting a target conductivity or target concentration of the substance to be reached at the end of the blood treatment;
- setting a blood treatment time;
- calculating the third parameter band taking into account the initial conductivity or initial concentration of the substance and target conductivity or target concentration of said substance.

In a 43$^{rd}$ aspect in accordance with any of the previous aspect 8 or 9, the fourth parameter is the heart rate and receiving or setting the prescription values of the fourth parameter comprises:

- setting a target heart rate to be reached at the end of the blood treatment; optionally, the target heart rate is a heart rate target band; measuring an initial heart rate of the patient; calculating the fourth parameter trajectory taking into account the initial heart rate and the target heart rate.

In a 44$^{th}$ aspect in accordance with the previous aspect 43, the target heart rate is a customized value for each patient and is read by, or entered in, the control unit.

In a 45$^{th}$ aspect in accordance with the previous aspect 43, the target heart rate is calculated by the control unit.

In a 46$^{th}$ aspect in accordance with the previous aspect 45, the target heart rate is calculated based on the initial measured heart rate of the patient and on an average heart rate reduction from literature data and/or anthropometric parameters of the patient.

In a 47$^{th}$ aspect in accordance with the previous aspect 46, the control unit is configured to record the fourth parameter trajectories of the treatments for each patient and to link each fourth parameter trajectory with a marker representative of patient well-being for each treatment.

In a 48$^{th}$ aspect in accordance with the previous aspect 47, the target heart rate is calculated based on the initial measured heart rate of the patient and on an average heart rate reduction from recorded fourth parameter trajectory linked with a positive marker.

In a 49$^{th}$ aspect in accordance with any of the previous aspects, the supply line comprises a dialysis line of a dialysis fluid connected to the inlet port of the second chamber and at least an infusion line of a replacement fluid connected with the extracorporeal blood circuit or directly connectable with the patient; optionally the infusion line and the dialysis line departs both from a same preparation line and the dialysis fluid and the replacement fluid are the same liquid prepared by said preparation line and crossing the supply line.

In a 50$^{th}$ aspect in accordance with the previous aspect 49, said parameters further comprises a fifth parameter relating to a parameter selected from: an infusion flow rate of a replacement fluid crossing the infusion line or a transmembrane pressure between the first chamber and the second chamber.

In a 51$^{st}$ aspect in accordance with the previous aspect 50, the control unit is configured to calculate a fifth parameter control value and to impose also the fifth parameter control value during the time interval consecutive to the instant in which the control is made such that:

- the actual values of the first parameter track the prescription values of the first parameter over the predetermined treatment time; and
- the actual values of the fourth parameter track the prescription values of the fourth parameter over the predetermined treatment time.

In a 52$^{nd}$ aspect in accordance with the previous aspects 51 and 37, the second regulating device are configured also to regulate a composition of the replacement fluid, the second regulating device being active on the infusion line for regulating the third parameter.

In a 53rd aspect according to any of the previous aspects, the actual values of the third parameter are values of concentration of at least sodium in the liquid crossing the supply line; wherein the control procedure uses a mathematical model, representing kinetics of the solutes in a distribution volume in the patient, in order to determine equivalent sodium concentration values, wherein by equivalent sodium concentration at instant t is intended the constant sodium concentration in the liquid crossing the supply line which, if it were applied at the start of treatment up to a certain instant t, would lead to the same plasma sodium concentration in the patient as is obtained at the same instant t with the variation in sodium concentration or conductivity imposed by the control procedure up to time t; the control procedure using the equivalent sodium concentration values as actual values of the third parameter for the determination of the control values.

In a 54th aspect according to the previous aspect, the prescription values of the third parameter are values of equivalent sodium concentration and the target sodium concentration is a target equivalent sodium concentration.

DESCRIPTION OF THE DRAWINGS

The invention will be described with the aid of the figures of the drawings, by way of non-limiting example, which illustrate some aspects of the invention.

In particular:

FIG. 2A is a flow diagram relating to the block diagram of FIG. 2;

FIG. 5A is a flow diagram relating to the block diagram of FIG. 5.

DETAILED DESCRIPTION

Figure 1:
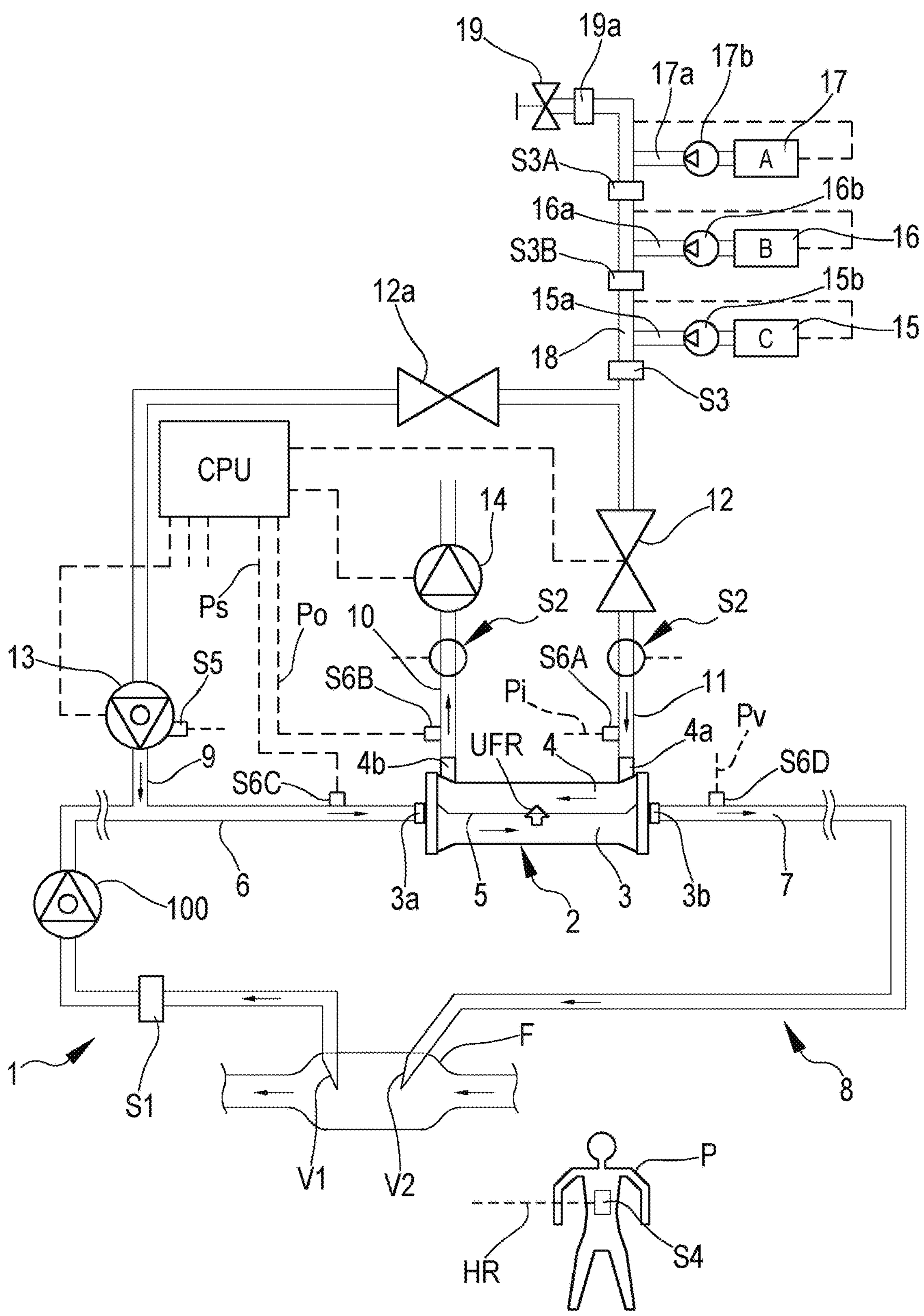
FIG. 1 is a schematic illustration of an example of a blood treatment apparatus of the invention.

With reference to FIG. 1, number 1 denotes in its entirety an apparatus for extracorporeal blood treatment. The apparatus 1 comprises at least one treatment unit 2, for example a hemofilter, a hemodiafilter, a plasma filter, having at least one first chamber 3 and at least one second chamber 4 separated from one another by a semipermeable membrane 5.

A blood removal line 6 is connected with an inlet port 3*a* of the first chamber 3 and is predisposed, in operating conditions of connection to a patient P, to remove blood from a vascular access V1 inserted for example in a fistula F of the patient P.

A blood return line 7 connected to an outlet port 3*b* of the first chamber 3 is predisposed to receive the treated blood from the treatment unit 2 and to return the treated blood to a further vascular access V2 connected with the patient's fistula. Note that the configuration of the vascular access may be of any nature: for example a catheter, a port implanted in the patient, a cannula, a needle, etc. The blood removal line 6, the first chamber 3 of the treatment unit 2 and the blood return line 7 to the patient P are part of an extracorporeal blood circuit 8. A blood pump 100 on the blood removal line 6, during the use of the apparatus 1, provides for the circulation of the blood externally of the patient's body when subjected to treatment.

In the example of FIG. 1, an infusion line 9 of a replacement fluid is connected to the blood removal line 6, upstream of the first chamber 3. Alternatively, the infusion line 9 might be connected to the return line 7, downstream of the first chamber 3. In other examples, an infusion line may be connected downstream while another infusion line may be connected upstream of the unit 2. Further infusion lines may also be provided, for example connected downstream and/or upstream of the treatment unit. The apparatus 1 further comprises at least one fluid evacuation line 10 connected with an outlet port 4*b* of the second chamber 4 for receiving at least a fluid filtered across the semipermeable membrane 5. A dialysis line 11 supplies a fresh treatment fluid to an inlet 4*a* of the second chamber 4. A fluid check organ 12 may be used to selectively enable or inhibit a passage of fluid across the dialysis line 11, according to whether it is desired, or not, to have a purification by diffusive effect internally of the treatment unit. In the example of FIG. 1, the dialysis line 11 and the infusion line 9 are part of a same supply line. The apparatus 1 comprises sensor devices for determining the actual values assumed during treatment by parameters described herein below. The apparatus 1 further comprises a control unit CPU connected with the sensor devices and configured to receive prescription values of said parameters to be reached in the patient P or to follow over a predetermined treatment time (T) and to obtain, through the sensor devices, the actual values of said parameters during the extracorporeal blood treatment. The apparatus 1 further comprises a user interface, not shown, provided with input and output devices, like a keyboard, a display, a touch screen, etc. connected to the control unit CPU.

Parameters

The following parameters are considered (prescribed and/or detected and/or adjusted) by the apparatus for extracorporeal blood treatment:

- a first parameter (BV %) relating to a variation in blood volume of the patient P;
- a second parameter (UFR; WLR; WL) relating to an ultrafiltration flow rate through the semipermeable membrane 5 or to a weight loss rate of the patient P or to an accumulated weight loss;
- a third parameter (Cd, Na) relating to a conductivity of a liquid crossing the dialysis line 11 and the infusion line 9 or to a concentration of a substance, optionally sodium and/or potassium or any other substance typically composing the dialysis fluid (e.g. bicarbonate, calcium, magnesium, etc.), in a liquid crossing the dialysis line 11 and the infusion line 9;
- a fourth parameter (HR; HRV) relating to heart rate of the patient P;
- a fifth parameter ($Q_{INF}$, TMP) relating to a parameter selected from: an infusion flow rate of a replacement fluid crossing the infusion line or a transmembrane pressure between the first chamber 3 and the second chamber 4.

There follows a description of sensor devices for each of the main parameters to be read.

First Parameter—Variation of Blood Volume

The sensor devices of the apparatus 1 comprise a first sensor S1 for detecting the actual values of the first parameter, e.g. variation of blood volume (BV %) or an actual value of a parameter from which the variation of blood volume (BV %) may be calculated in relation to the blood of a patient P subjected to treatment. The blood volume variation sensor S1 may for example be optical and able to detect a variation in the optical properties of the blood crossing a calibrated portion of tube. For instance, a blood volume variation sensor S1 may calculate, through the control unit CPU, a percentage variation of the blood volume (BV %) circulating in the patient from start of hemodialysis treatment (or hemofiltration, or hemodiafiltration) based on the measurement of the concentration of haemoglobin in the blood, according to the known formula: BV % (t)=($HGB_0/HGB_t$)−1, where $HGB_0$ represents the concentration of haemoglobin at start of treatment and $HGB_t$ the concentration of haemoglobin at time tin which variation of the blood volume (BV %) is calculated. The haemoglobin concentration is calculated based on the variation of optic absorbance, at a predetermined wavelength, of the blood flowing in the blood removal line 6, across a tract of tube having the appropriate optical properties, previously characterised.

Second Parameter—Ultrafiltration Flow Rate

The sensor devices of the apparatus 1 comprise at least a second sensor S2 for detecting the actual values of the ultrafiltration flow rate (UFR; second parameter) across the semipermeable membrane 5. For example, a flow sensor S2 may be active on the evacuation line 10 and a flow sensor S2 on the dialysis line 11 such as to provide the control unit CPU with the instant value of the respective flows and thus enable the control unit CPU to calculate an instant ultrafiltration flow. Alternatively, a differential sensor may be provided, active on the evacuation line 10 and dialysis line 11 and therefore able directly to provide a signal relating to the ultrafiltration flow rate UFR.

The sensor or sensors S2 may be volumetric sensors, mass sensors such as for example Coriolis sensors, weight sensors such as for example scales, pump revolution sensors, or sensors of yet another type: as the type of sensors usable is not significant and since the techniques and the sensors for detecting absolute or differential flow values are known and within the experience of the expert person in the field, no further details thereof are included in the present text.

Second Parameter—Weight Loss Rate

The weight loss rate (WLR; second parameter) may be measured by subtracting the infusion rate (for example as described thereafter) from the ultrafiltration flow rate (for example as described above) as UFR=$Q_{INF}$+WLR. As a further alternative, a sensor may be provided which is able directly to provide a signal which gives the weight loss rate (WLR): for example a sensor able to differentially measure the rate taken from the evacuation line 10 and to subtract the flow rate crossing the dialysis line 11 and/or the rate or rates of infusion 9. The sensor may be a mass flow sensor (for example a Coriolis sensor), volumetric, electromagnetic, ponderal (such as a scales able to weigh bags of fluid) or another type.

Second Parameter—Weight Loss

The apparatus 1 may also determine the weight loss (WL; second parameter) over a time period, for example from start of the treatment up to an instant t: for example the control unit CPU may be programmed to integrate the weight loss rate (WLR) over the time. Alternatively, a weight loss sensor may be provided, for example a sensor configured to detect the variation in overall weight of a patient P during treatment or a sensor destined to directly detect the overall weight of the net fluid extracted from the patient P.

Third Parameter—Conductivity or Substance Concentration

The sensor devices of the apparatus 1 further comprise at least a third sensor S3 for detecting the actual values of the third parameter, i.e. conductivity or sodium concentration or another substance, like potassium, that is to be monitored of the liquid crossing the dialysis line 11 and/or the infusion line 9. For instance, the conductivity or concentration sensor S3 may be located immediately downstream of a device for regulating a composition of dialysis liquid and/or replacement fluid, which will be more fully described in the following.

The apparatus 1 may also not comprise a conductivity or concentration sensor directly acting on the patient or on the extracorporeal blood circuit. In this case, the control procedure uses a mathematical model M representing a kinetics of solutes in a distribution volume V in the patient for iteratively calculating, at each control instant t, an equivalent sodium concentration value $Na_{eq(t)}$. Note that by equivalent sodium concentration at instant t ($Na_{eq(t)}$) reference is made to the constant sodium concentration in the dialysis liquid that, if applied at the start of treatment up to a certain instant t, would lead to the same plasma sodium concentration in the patient as is obtained at the same instant t with the variation of sodium concentration or conductivity set by the control procedure up to time t. In this case, also the prescription values of sodium concentration are prescription values of equivalent sodium concentration.

Fourth Parameter—Heart Rate or Variation of Heart Rate

The sensor devices of the apparatus 1 further comprise at least a fourth sensor S4 for detecting the actual values of the fourth parameter, i.e. heart signal, rate (HR) and/or variation of heart rate (HRV) of the patient P. The heart rate (HR) of the patient P is monitored continuously and in real time, e.g. through a patch sensor, a wristband or an armband sensor, a chest strap sensor, a wearable electrode based ECG, a touch device, a breathable heart rate monitor, a contactless sensor, an ingestible pill sensor. The heart signal may also be monitored through a sensor on the blood line or lines. The detected actual value of the heart rate may be an average of heart rate (HR) over a time interval, e.g. 10 s. The variation of heart rate or heart rate variability (HRV) is the physiological phenomenon of the variation in the time interval between consecutive heartbeats and may be calculated in real time from the heart signal. The variation of heart rate (HRV) may be calculated at each heartbeat or may be an average calculated over a plurality of heartbeats, e.g. 10 heartbeats. The variation of heart rate (HRV) may be calculated through known methods, like: time domain methods or geometric methods or frequency-domain methods or non-linear methods.

Fifth Parameter—Infusion Flow Rate

The sensor devices of the apparatus 1 further comprise at least a fifth sensor S5 for detecting the actual values of the infusion flow rate ($Q_{INF}$; fifth parameter) of the replacement fluid crossing the infusion line 9. The fifth sensor or sensors S5 may be volumetric sensor/s, mass sensor/s such as for example Coriolis sensor/s, weight sensor/s such as for example scales, pump revolution sensor/s or sensor/s of still other types: as the type of sensors usable is not significant and since the techniques and the sensors for detecting absolute or differential flow values are known and within the experience of the expert person in the field, no further details thereof are included in the present text. In the case illustrated in FIG. 1, the infusion flow rate sensor S5 is configured to determine a number of revolutions of an infusion pump 13, by sending a corresponding signal to the control unit CPU which is configured such as to calculate a flow rate along the respective infusion line 9.

Fifth Parameter—Transmembrane Pressure

A sixth sensor may be configured to measure the transmembrane pressure (TMP; fifth parameter). During treatment fluid and undesired particles are moved from the first chamber 3 towards the second chamber 4 of the treatment unit 2. The fluid and/or particle movement creates a transmembrane pressure which is defined as the mean pressure applied on the side of the first chamber towards the side of the second chamber. The transmembrane pressure (TMP) may be determined in various modes. For example, if (see FIG. 1) four sixth pressure sensors are present, of which one S6A is on the dialysis line 11, another S6B on the evacuation line 10, another S6C on the blood removal line 6 and a another S6D on the return line 7, the transmembrane pressure (TMP) actual value is determined by the control unit CPU using the pressure signals coming from sensors from S6A to S6D, using the formula:

$$TMP = \frac{Ps + Pv}{2} - \frac{Pi + Po}{2}$$

where:

Pi is the pressure detected by sensor S6A
Po is the pressure detected by sensor S6B
Ps is the pressure detected by sensor S6C
Pv is the pressure detected by sensor S6D The apparatus 1 comprises regulating devices for regulating the second parameter and the third parameter.

First Regulating Device

The apparatus 1 comprises a first regulating device for regulating the second parameter. The first regulating device are connected to the control unit CPU and are active on at least one of the extracorporeal blood circuit 8 and the fluid evacuation line 10. In the example of FIG. 1, the first regulating device comprises an ultrafiltration pump 14 located on the fluid evacuation line 10 and able to recall fluid from the second chamber 4. In other embodiments, the first regulating device may comprise two pumps piloted differentially, such as two blood pumps located one upstream and one downstream of the treatment unit 2, or a plurality of pumps located on the lines and piloted such as to create an ultrafiltration flow across the membrane 5 or combinations of one or more pumps and valves appropriately arranged on the blood lines 6, 7 or fluid evacuation line 10. The control unit CPU is connected to the first regulating device to pilot the pump or pumps such as to adjust the ultrafiltration flow rate (UFR) as will be detailed thereafter.

Second Regulating Device

The apparatus 1 further comprises a second regulating device for regulating the third parameter, i.e. the composition of the dialysis liquid and/or of the replacement fluid.

In the example of FIG. 1, the second regulating device comprises one, two or more containers of concentrate 15, 16, 17 located on respective injection lines 15*a*, 16*a*, 17*a* which are predisposed to supply substances such as electrolytes, buffer agents or others towards a preparation line 18 of the liquid located upstream of the dialysis line 11. The concentrate containers 15, 16, 17 may comprise concentrates in the liquid state or solid state, for example powder. Injection pumps 15*b*, 16*b*, 17*b* may be present on the injection lines 15*a*, 16*a*, 17*a* to move the fluid along the respective injection line towards the preparation line 18 which collects the liquid, for example water, from a source 19. The source 19 may comprise a water tap or a source of ultra-pure liquid. The water collected from the source and possibly subjected to filtering stages 19*a* (not detailed as known and not relevant to the present invention) is provided with the necessary substances.

According to the embodiment shown in FIG. 1, the supply line comprises the infusion line 9 and the dialysis line 11 which depart both from the preparation line 18. Therefore, the dialysis fluid and the replacement fluid are the same liquid prepared by the preparation line 18 liquid and crossing the supply line. A further fluid check organ 12*a* may also be used to selectively enable or inhibit a passage of fluid across the infusion line 9.

The concentration or conductivity sensor S3, possibly added-to by further concentration or conductivity sensors S3A, S3B located on the preparation line 18, is able to provide the control unit CPU with a relative signal of conductivity or concentration of a predetermined substance (for example sodium and/or potassium) of the fluid crossing the preparation line 18 such that the control unit CPU may act on the second regulating device and in particular on the pumps 15*b*, 16*b*, 17*b* in order to regulate the conductivity (Cd) or concentration, for example of sodium (Na) or potassium (K), of the liquid crossing the dialysis line 11 and/or the infusion line 9.

The infusion line 9 may also collect the fluid from a further source (for example a bag containing replacement fluid, not shown) independent with respect to the water source 19, while the preparation line 18 exclusively supplies the dialysis line 11 of the dialysis liquid.

Figure 2:
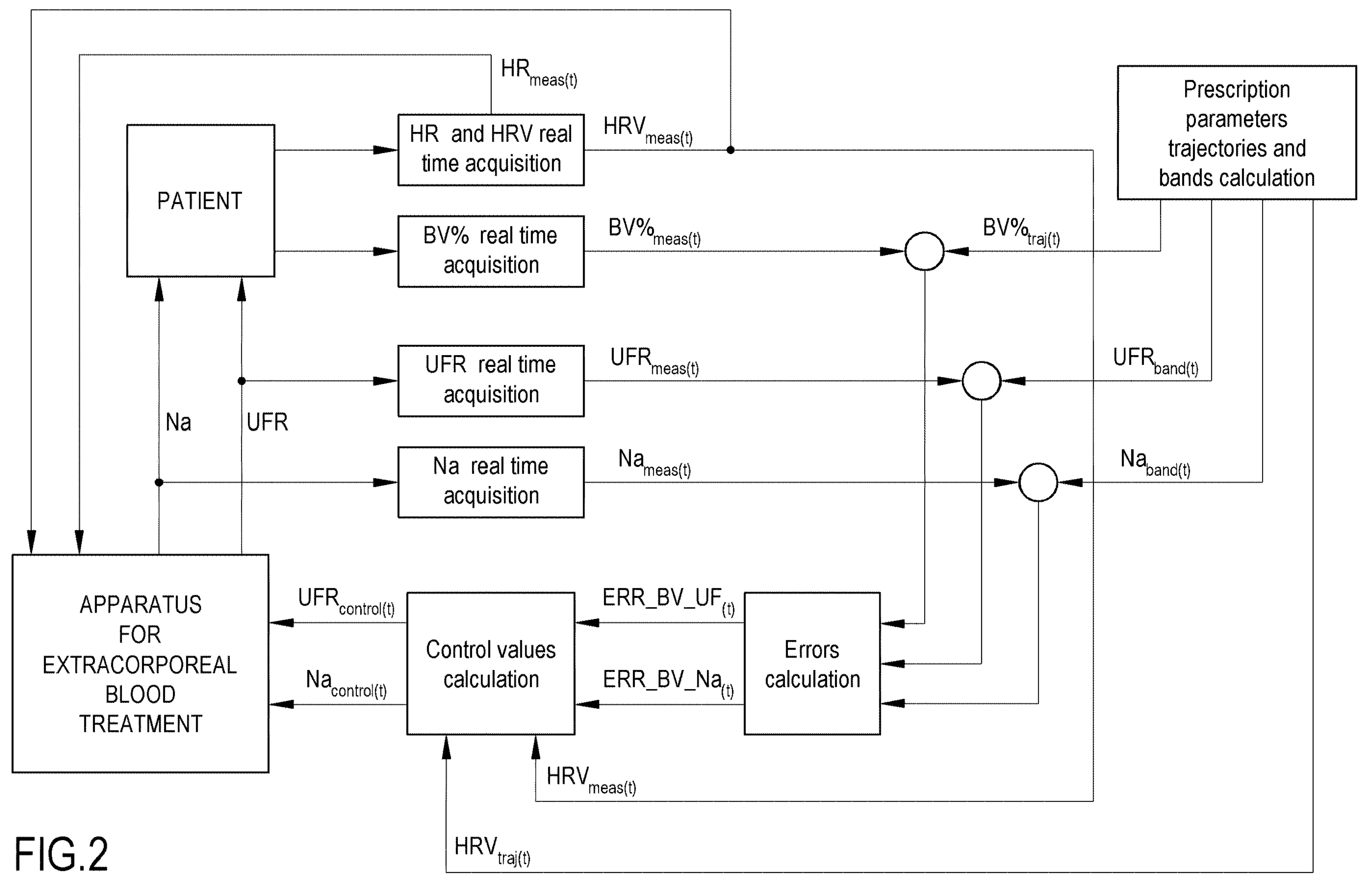
FIG. 2 is a block diagram relating to a first embodiment of a control procedure of the invention.
Figure 3:
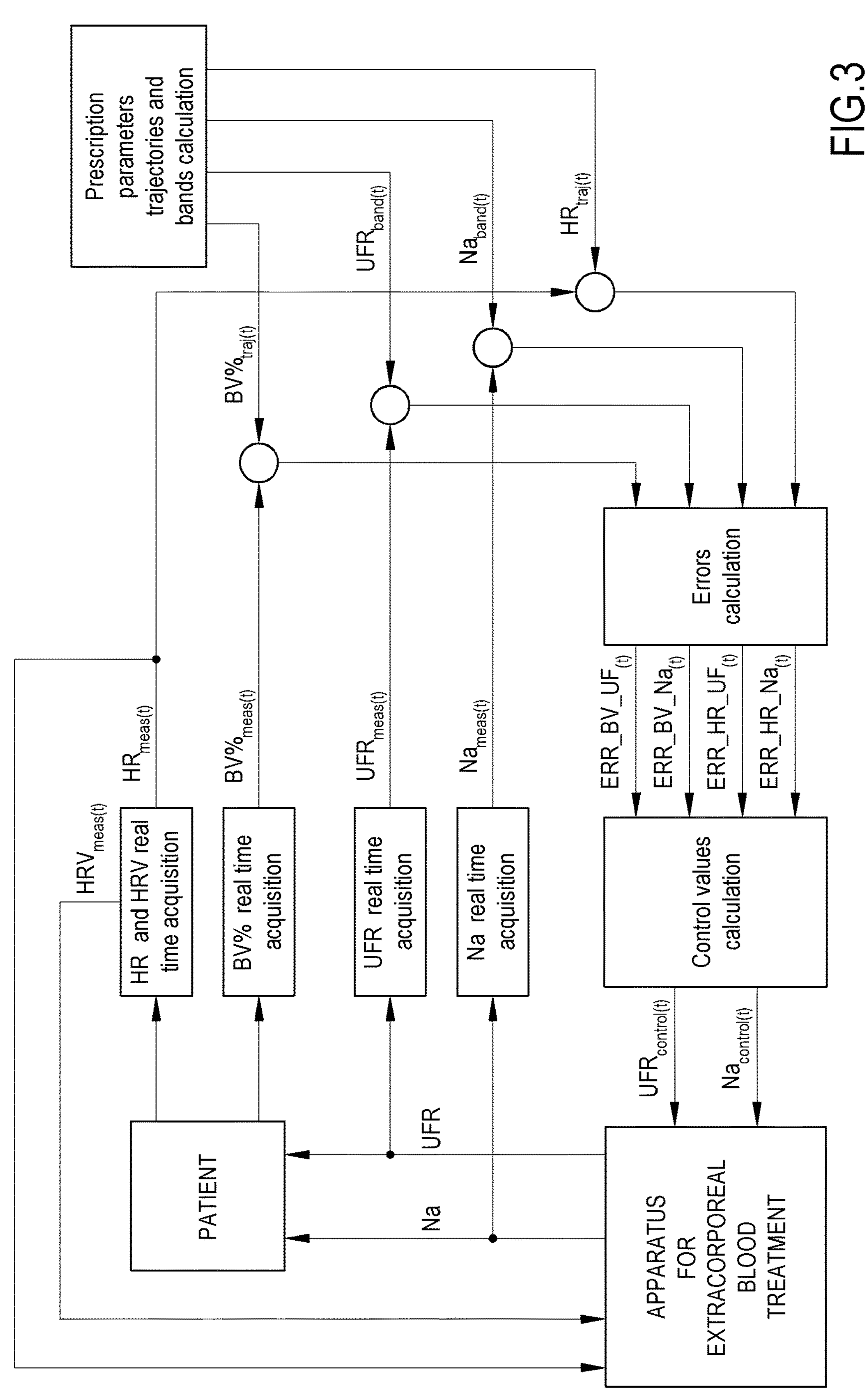
FIG. 3 is a block diagram relating to a second embodiment of the control procedure of the invention.

Control Procedure—FIGS. 2 and 3

The control unit CPU may comprise one or more digital units, for example microprocessors, or one or more analog units, or a special combination of digital and analog units. The control unit CPU is connected with the first and the second regulating devices, with the user interface, with the sensor devices and with the various actuator organs (blood pump 100, infusion pump 13, ultrafiltration pump 14, fluid check organ 12) located along the lines 6, 9, 10, 11 and is configured or programmed to perform the procedures described herein. In a case in which the control unit CPU is programmable, the control unit CPU is connected with a data support for storing instructions which, when performed by the control unit CPU, determine performing of the procedures which will be described herein below. The data support may comprise a mass data memory, for example optical or magnetic, a re-programmable memory (EPROM, FLASH) or a memory of another nature.

In an aspect of the invention, the control unit CPU is programmed or configured such as to perform a control procedure comprising the steps described herein below.

The control procedure and the method actuated by said control procedure allow to reduce and/or prevent hypotension occurrences in patients undergoing extracorporeal blood treatment due not only to osmolality reduction but also to cardiac dysfunctions during the treatment.

According to an example, in a first step, the control unit CPU receives, for instance via the user interface:

- a blood treatment time (T),
- an estimated or measured initial concentration of haemoglobin and/or an initial blood volume ($BV_{init}$) of the patient;
- an estimated or measured initial conductivity or an initial sodium concentration ($Cd_{init}$, $Na_{init}$) of the patient;
- a target variation in blood volume ($BV\ \%_{target}$) to be reached at the end of the blood treatment;
- a target ultrafiltration volume ($UF_{target}$) or target weight loss ($WL_{target}$) to be reached at the end of the blood treatment;
- a target conductivity or target sodium concentration ($Cd_{target}$, $Na_{target}$) to be reached at the end of the blood treatment, optionally a target equivalent sodium concentration;
- a heart rate trajectory ($HR_{traj(t)}$) or a threshold of variation of heart rate ($HRV_{traj(t)}$).

Figures 4A, 4B:
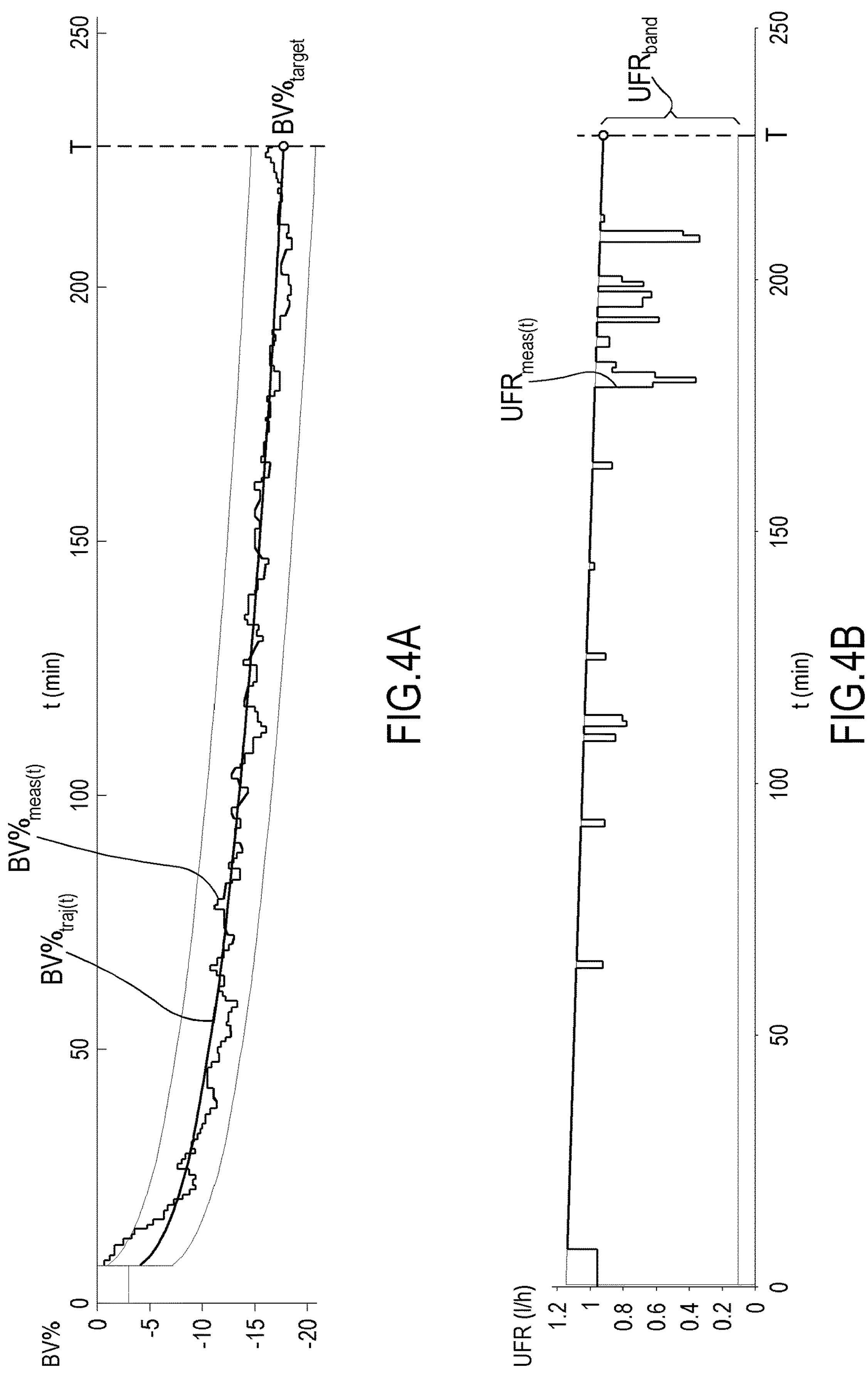
FIGS. 4A to 4E show the progression of parameters of the extracorporeal blood treatment controlled through the control procedure of the invention.

The control unit CPU calculates a first parameter trajectory ($BV\ \%_{traj(t)}$) from the estimated or measured initial concentration of haemoglobin and/or an initial blood volume of the patient P, the target variation in blood volume ($BV\ \%_{target}$) and the treatment time (T). The control unit CPU also calculates a first parameter band delimited between an upper trajectory (above the first parameter trajectory ($BV\ \%_{traj(t)}$)) and a lower trajectory (below the first parameter trajectory ($BV\ \%_{traj(t)}$)), wherein a mid-line of the first parameter band defines said first parameter trajectory ($BV\ \%_{traj(t)}$). As shown in FIG. 4A, the first parameter trajectory ($BV\ \%_{traj(t)}$) comprises a succession of prescription values of the variation in blood volume (BV %) to be followed over the treatment time. Usually, the first parameter trajectory ($BV\ \%_{traj(t)}$) decreases over treatment time. The mid line of the fourth parameter band shown in FIG. 4A is in the middle, i.e. equally spaced from the upper trajectory and lower trajectory, but said mid line may also be eccentric compared to the upper trajectory and lower trajectory.

The control unit CPU calculates, from the target ultrafiltration volume ($UF_{target}$) or target weight loss ($WL_{target}$) and the treatment time (T), a second parameter band or ultrafiltration flow rate band ($UFR_{band}$) delimited between an upper trajectory and a lower trajectory over the treatment time. Usually, the upper trajectory and a lower trajectory are straight lines slightly decreasing and converging one towards the other over treatment time, like in FIG. 4B. The points of the upper trajectory and the lower trajectory and comprised between the upper trajectory and the lower trajectory are prescription values of the UFR. The control unit CPU calculates, from the estimated or measured initial conductivity or an initial sodium concentration, the target conductivity or target sodium concentration and the treatment time (T), a third parameter band or conductivity or sodium concentration band ($Cd_{band}$, $Na_{band}$) delimited between an upper trajectory and a lower trajectory over the treatment time. Usually, the upper trajectory and the lower trajectory are straight lines slightly decreasing and converging one towards the other over treatment time, like in FIG. 4C. The points of the upper trajectory and the lower trajectory and comprised between the upper trajectory and the lower trajectory are prescription values of the Cd or Na.

Figures 4C, 4D:
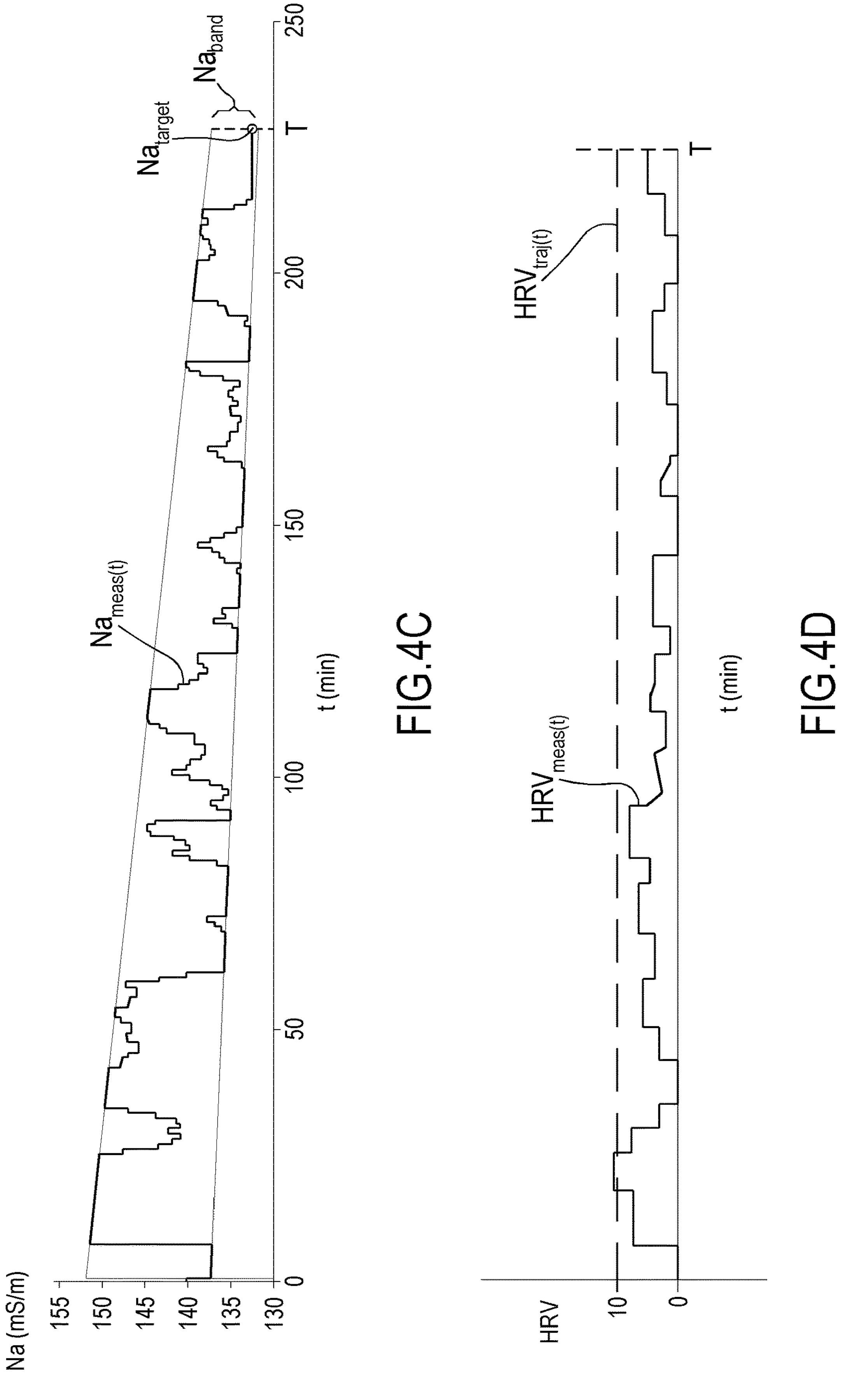
Figure 4E:
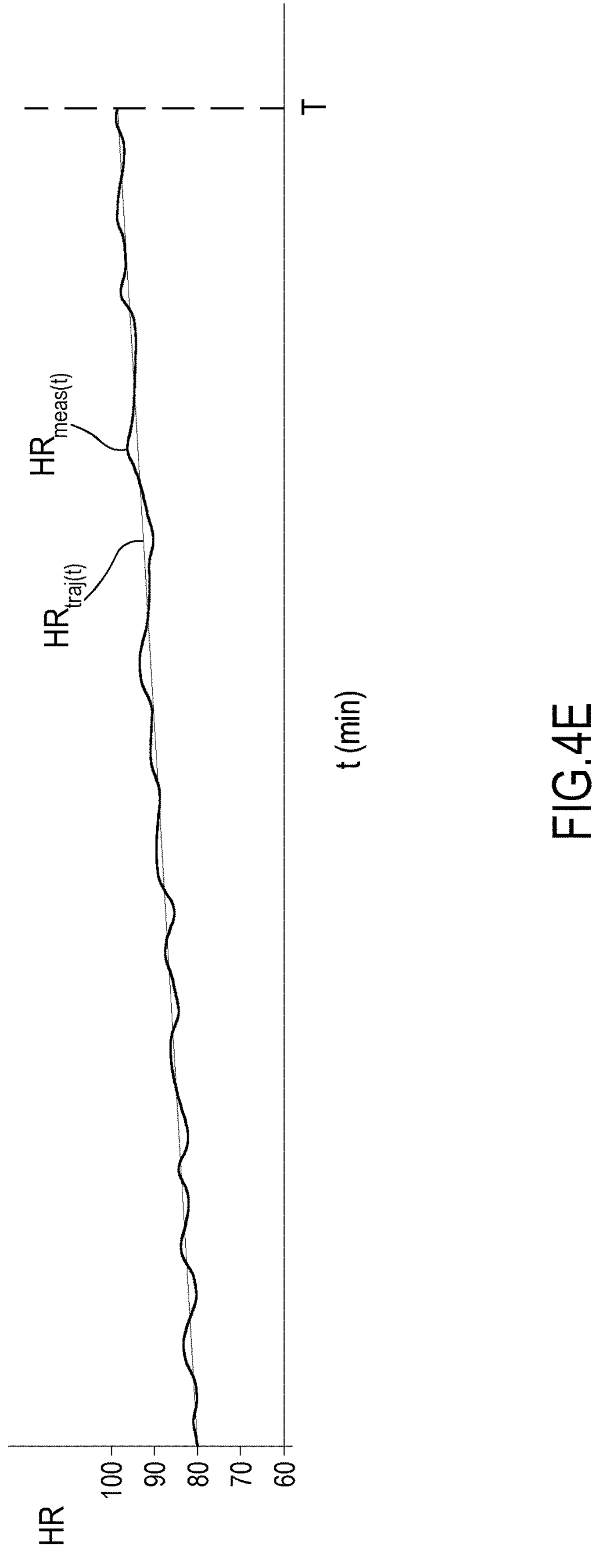

The control unit CPU further calculates a fourth parameter trajectory ($HR_{traj(t)}$, $HRV_{traj(t)}$) defining prescription values of the fourth parameter (FIG. 4D or 4E) over treatment time. The fourth parameter trajectory may be a trajectory of heart rate ($HR_{traj(t)}$), shown in FIG. 4E, or a trajectory of variation of heart rate ($HRV_{traj(t)}$), shown in FIG. 4D. If the fourth parameter trajectory is variation of heart rate ($HRV_{traj(t)}$), this may be constant over time and defining un upper threshold of variation of heart rate of the patient which should not be exceeded during blood treatment (FIG. 4D). If the fourth parameter trajectory is heart rate ($HR_{traj(t)}$), this may be a straight line increasing over treatment time and which should be followed by the heart rate of the patient P during blood treatment (FIG. 4E). Generally speaking, the prescription values of the fourth parameter linked to the heart rate may be: a trajectory to be followed by the actual values of the fourth parameter, a threshold which the actual values of the fourth parameter should not exceed, a band delimited by un upper and a lower trajectory or threshold and which the actual values of the fourth parameter should be kept inside. Blood treatment is started and the control unit CPU receives continuously and in real time during treatment (real time acquisition):

- the actual values of the variation of blood volume ($BV\ \%_{meas(t)}$) from the first sensor S1 (FIG. 4A);
- the actual values of the ultrafiltration flow rate ($UFR_{meas(t)}$) from the second sensor S2 (FIG. 4B);
- the actual values of the conductivity or sodium concentration ($Cd_{meas(t)}$, $Na_{meas(t)}$) from the third sensor S3 (FIG. 4C);
- the actual values of the heart rate ($HR_{meas(t)}$) from the fourth sensor S4 (FIG. 4E) and may also calculate the actual values of the variation of heart rate ($HRV_{meas(t)}$) (FIG. 4D).

The control unit CPU calculates, at temporally consecutive control instants and on the basis of the actual values and of the prescription values, the following control values to be set during a time interval after the instant in which the control is made:

- a second parameter control value, i.e. ultrafiltration flow rate control value ($UFR_{control(t)}$); and/or
- a third parameter control value, i.e. conductivity or sodium concentration control value ($Cd_{control(t)}$; $Na_{control(t)}$).

The control unit CPU commands the ultrafiltration pump 14 (first regulating device) to impose the ultrafiltration flow rate control value ($UFR_{control(t)}$) during a time interval consecutive to the instant in which the control is made. In other words, the ultrafiltration pump 14 is adjusted such that the actual value of the ultrafiltration flow rate $UFR_{meas(t+\alpha t)}$ at the time interval after the instant in which the control is made is equal or close to the ultrafiltration flow rate control value ($UFR_{control(t)}$). The control unit CPU commands the injection pumps 15_b_, 16_b_, 17_b_ (second regulating device) to impose the conductivity or sodium concentration control value ($Cd_{control(t)}$; $Na_{control(t)}$) during a time interval consecutive to the instant in which the control is made. In other words, the injection pumps 15*b*, 16*b*, 17*b* are adjusted such that the actual values of the conductivity or sodium concentration ($Cd_{meas(t+\alpha t)}$, $Na_{meas(t+\alpha t)}$) at the time interval after the instant in which the control is made is equal or close to the conductivity or sodium concentration control value ($Cd_{control(t)}$; $Na_{control(t)}$).

The ultrafiltration flow rate control value ($UFR_{control(t)}$) and the conductivity or sodium concentration control value ($Cd_{control(t)}$; $Na_{control(t)}$) are calculated and imposed such that the actual values of the variation of blood volume (BV $\%_{meas(t)}$) track the prescription values of the variation of blood volume (first parameter trajectory BV $\%_{traj(t)}$) over the predetermined treatment time (T) and the actual values of the heart rate ($HR_{meas(t)}$) or of the variation of heart rate ($HRV_{meas(t)}$) track the prescription values of the heart rate or of the variation of heart rate (fourth parameter trajectory) over the predetermined treatment time (T).

For instance, the ultrafiltration flow rate control value ($UFR_{control(t)}$) and the conductivity or sodium concentration control value ($Cd_{control(t)}$; $Na_{control(t)}$) are calculated and imposed such that the values of the variation of blood volume (BV $\%_{meas(t)}$) follows the prescribed trajectory or is kept in a neighbourhood of said the prescribed trajectory or within the prescribed band (BV $\%_{traj(t)}$, FIG. 4A). The ultrafiltration flow rate control value ($UFR_{control(t)}$) and the conductivity or sodium concentration control value ($Cd_{control(t)}$; $Na_{control(t)}$) are also calculated and imposed such that the actual values of the variation of heart rate ($HRV_{meas(t)}$) do not exceed the prescribed threshold ($HRV_{traj(t)}$, FIG. 4D) and/or the actual values of the heart rate ($HR_{meas(t)}$) follow the prescribed trajectory ($HR_{traj(t)}$, FIG. 4E).

According to embodiments, the control unit CPU is configured or programmed first to impose only the conductivity or sodium concentration control value ($Cd_{control(t)}$; $Na_{control(t)}$) to track the prescription values of the variation of blood volume, of the heart rate or of the variation of heart rate and then, if the cited prescription values are not tracked correctly, to impose also the ultrafiltration flow rate control value ($UFR_{control(t)}$).

In addition, the ultrafiltration flow rate control value a ($UFR_{control(t)}$; $WLR_{control(t)}$; $WL_{control(t)}$) is calculated to be within the ultrafiltration flow rate band ($UFR_{band}$) and the conductivity or sodium concentration control value is calculated to be within the conductivity or sodium concentration band ($Cd_{band}$, $Na_{band}$), i.e. to keep the respective actual values within the respective bands, as shown in FIGS. 4B and 4C. The ultrafiltration flow rate control value ($UFR_{control(t)}$; $WLR_{control(t)}$; $WL_{control(t)}$) and/or the conductivity or sodium concentration control value ($Cd_{control(t)}$; $Na_{control(t)}$) may also be null, i.e. the control unit CPU may stop ultrafiltration and/or sodium administration.

The control values ($UFR_{control(t)}$; $Cd_{control(t)}$; $Na_{control(t)}$) may be calculated in different ways.

1st Embodiment—FIGS. 2 and 2A

According to a 1st embodiment, the control unit CPU determines a first error parameter ($ERR\_BV\_UF_{(t)}$) on the basis of a difference between the actual value of the variation of blood volume (BV $\%_{meas(t)}$) at the control instant (t) and a corresponding value on the first parameter trajectory (BV $\%_{traj(t)}$) and a difference between an actual value of the second parameter ($UFR_{meas(t)}$; $WLR_{meas(t)}$; $WL_{meas(t)}$) at the control instant (t) and a corresponding value of the second parameter band. The control unit CPU determines a second error parameter ($ERR\_BV\_Na_{(t)}$) on the basis of a difference between the actual value of the variation of blood volume (BV $\%_{meas(t)}$) at the control instant (t) and a corresponding value on the first parameter trajectory (BV $\%_{traj(t)}$) and a difference between an actual value of the third parameter ($Cd_{meas(t)}$; $Na_{meas(t)}$) at the control instant (t) and a corresponding value of the third parameter band.

Then, the control unit CPU calculates a first value of the second parameter control value ($UFR_{control(t)}$; $WLR_{control(t)}$; $WL_{control(t)}$) on the basis of the first error parameter ($ERR\_BV\%\_UF_{(t)}$) and of the actual value of the second parameter ($UFR_{meas(t-\Delta t)}$; $WLR_{meas(t-\Delta t)}$; $WL_{meas(t-\Delta t)}$)) relating to a preceding control instant and calculates a first value of the third parameter control value ($Cd_{control(t)}$; $Na_{control(t)}$) on the basis of the second error parameter ($ERR\_BV\%\_Na_{(t)}$) and of the actual value of the third parameter ($Cd_{meas(t-\Delta t)}$, $Na_{meas(t-\Delta t)}$) relating to a preceding control instant. Then said first values of the second parameter control value ($UFR_{control(t)}$; $WLR_{control(t)}$; $WL_{control(t)}$) and/or of the third parameter control value ($Cd_{control(t)}$; $Na_{control(t)}$) are corrected on the basis of the actual values ($HRV_{meas(t)}$) and of the prescription values (prescribed threshold $HRV_{traj(t)}$) of the variation of heart rate HRV (fourth parameter).

If the first values of the second parameter control value ($UFR_{control(t)}$; $WLR_{control(t)}$; $WL_{control(t)}$) and of the third parameter control value ($Cd_{control(t)}$; $Na_{control(t)}$) are proper to keep the actual values of the variation of blood volume (BV $\%_{meas(t)}$) on or close to the prescribed trajectory but the actual value of the variation of heart rate ($HRV_{meas(t)}$) is above the fourth parameter threshold, then said first values of the second parameter control value ($UFR_{control(t)}$; $WLR_{control(t)}$; $WL_{control(t)}$) and/or of the third parameter control value ($Cd_{control(t)}$; $Na_{control(t)}$) are further changed/corrected such to bring again the actual values of the variation of heart rate ($HRV_{meas(t)}$) below the fourth parameter threshold.

The actual value of the variation of heart rate ($HRV_{meas(t)}$) may be compared with the prescription value of the variation of heart rate ($HRV_{traj(t)}$) at the instant (t) in which the control is made and the second and third parameter control values to be imposed during the time interval (Δt) consecutive to the instant (t) are corrected or recalculated as a function of said comparison.

For instance, the second parameter control value ($UFR_{control(t)}$; $WLR_{control(t)}$; $WL_{control(t)}$) and/or the third parameter control value ($Cd_{control(t)}$; $Na_{control(t)}$) are decreased with respect to their respective calculated first values in order to limit the variation of heart rate ($HRV_{meas(t)}$) and to keep it below the fourth parameter threshold.

According to this 1st embodiment, as shown in FIG. 2, the actual values of variation of heart rate ($HRV_{meas(t)}$) are also sent to the control unit CPU to be displayed on the display of the user interface of the apparatus while the actual values of heart rate ($HR_{meas(t)}$) are detected but not used in the control procedure disclosed above. Said actual values of heart rate ($HR_{meas(t)}$) are sent to the control unit CPU and displayed on the display of the user interface of the apparatus.

Figure 3A:
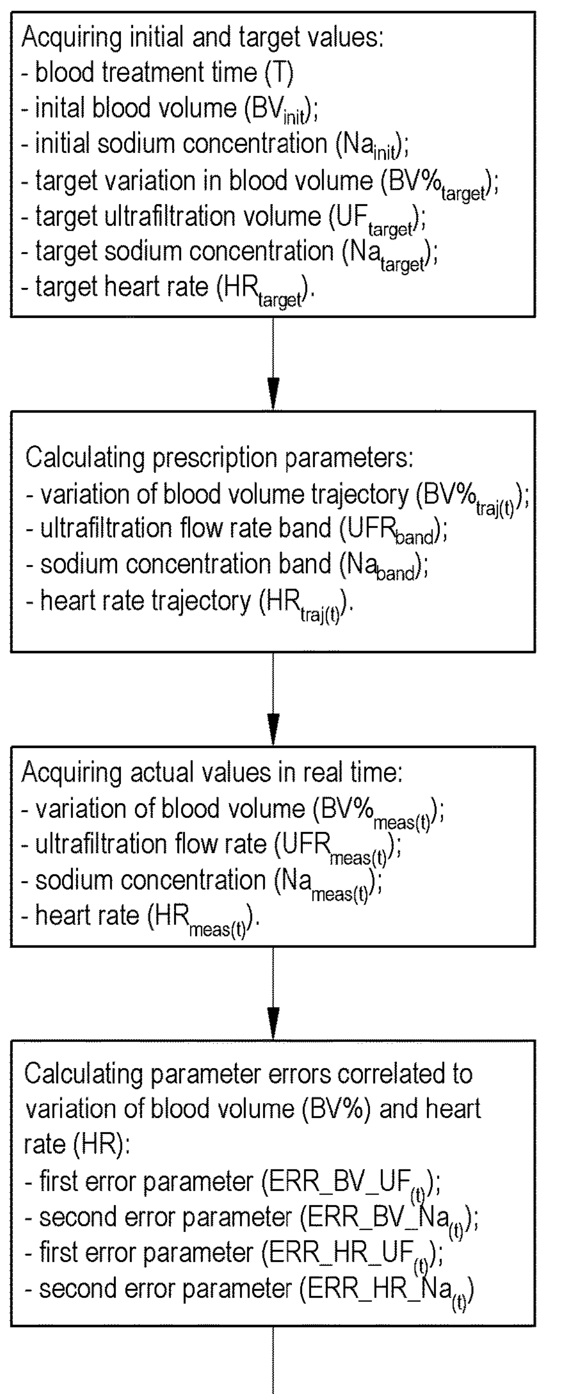
FIG. 3A is a flow diagram relating to the block diagram of FIG. 3.

2nd Embodiment—FIGS. 3 and 3A

According to a second embodiment, the fourth parameter is heart rate (HR) and not variation of heart rate (HRV). The control unit CPU receives an initial measured heart rate ($HR_{init}$) of the patient P and a target heart rate ($HR_{target}$) to be reached at the end of the blood treatment and customized for the patient P. The target heart ($HR_{target}$) rate may be calculated by the control unit CPU and may be based on the initial measured heart rate ($HR_{init}$) and on the literature data and/or anthropometric parameters of the patient P. The target heart rate may calculated based on the initial measured heart rate of the patient and on a wanted/prescribed heart rate reduction (e.g. from 80 bpm to 60 pbm): the patient starts treatment having 80 bpm and is stabilized around 60 bpm. The wanted/prescribed heart rate reduction may be an average. The target heart ($HR_{target}$) rate may also be a heart rate target band.

The control unit CPU calculates a heart rate trajectory ($HR_{traj(t)}$) (fourth parameter trajectory) over treatment time T taking into account the initial heart rate ($HR_{init}$) and the target heart rate ($HR_{target}$). The control unit CPU may also be configured to record the heart rate trajectories ($HR_{traj(t)}$) of the treatments for each patient, to link each heart rate trajectory ($HR_{traj(t)}$) with a marker representative of patient well-being for each treatment and to use said heart rate trajectories ($HR_{traj(t)}$) to calculate and update the heart rate trajectory ($HR_{traj(t)}$) for each new treatment. The heart rate trajectory ($HR_{traj(t)}$) may be a band. For instance, the heart rate band may be comprised between 40 and 70 heartbeats per minute.

In this $2^{nd}$ embodiment, the control unit CPU determines the first error parameter ($ERR\_BV\_UF_{(t)}$) and the second error parameter (ERR_BV_Na(t)) correlated to the variation of blood volume (BV %) as in the $1^{st}$ embodiment.

In addition, the control unit CPU determines a first error parameter ($ERR\_BV\_UF_{(t)}$) and a second error parameter ($ERR\_HR\_Na_{(t)}$) correlated to the heart rate HR.

The control unit CPU determines the first error parameter ($ERR\_BV\_UF_{(t)}$) correlated to the heart rate HR on the basis of a difference between the actual value of the heart rate ($HR_{meas(t)}$) at the control instant (t) and a corresponding value on the fourth parameter trajectory ($HR_{traj(t)}$) and a difference between an actual value of the second parameter ($UFR_{meas(t)}$; $WLR_{meas(t)}$; $WL_{meas(t)}$) at the control instant (t) and a corresponding value of the second parameter band.

The control unit CPU determines the second error parameter ($ERR\_HR\_Na_{(t)}$) correlated to the heart rate HR on the basis of a difference between the actual value of the variation of the heart rate ($HR_{meas(t)}$) at the control instant (t) and a corresponding value on the fourth parameter trajectory ($HR_{traj(t)}$) and a difference between an actual value of the third parameter ($Cd_{meas(t)}$; $Na_{meas(t)}$) at the control instant (t) and a corresponding value of the third parameter band.

Then, the control unit CPU calculates the second parameter control value ($UFR_{control(t)}$; $WLR_{control(t)}$; $WL_{control(t)}$) on the basis of two parameter errors: the first error parameter ($ERR\_BV\ \%\_UF_{(t)}$) correlated to the variation of blood volume (BV %), the first error parameter ($ERR\_HR\_UF_{(t)}$) correlated to the heart rate HR and of the actual value of the second parameter ($UFR_{meas(t-\Delta t)}$; $WLR_{meas(t-\Delta t)}$; $WL_{meas(t-\Delta t)}$)) relating to a preceding control instant.

The control unit CPU also calculates the third parameter control value ($Cd_{control(t)}$; $Na_{control(t)}$) on the basis of two parameter errors: the second error parameter ($ERR\_BV\ \%\_Na_{(t)}$) correlated to the variation of blood volume (BV %), the second error parameter ($ERR\_HR\_Na_{(t)}$) correlated to the heart rate (HR) and of the actual value of the third parameter ($Cd_{meas(t-\Delta t)}$, $Na_{meas(t-\Delta t)}$) relating to a preceding control instant.

According to this $2^{nd}$ embodiment, as shown in FIG. 3, the actual values of heart rate ($HR_{meas(t)}$) are also sent to the control unit CPU to be displayed on the display of the user interface of the apparatus while the actual values of variation of heart rate ($HRV_{meas(t)}$) are detected but not used in the control procedure disclosed above. Said actual values of variation of heart rate ($HRV_{meas(t)}$) are sent to the control unit CPU and displayed on the display of the user interface of the apparatus.

Figure 5:
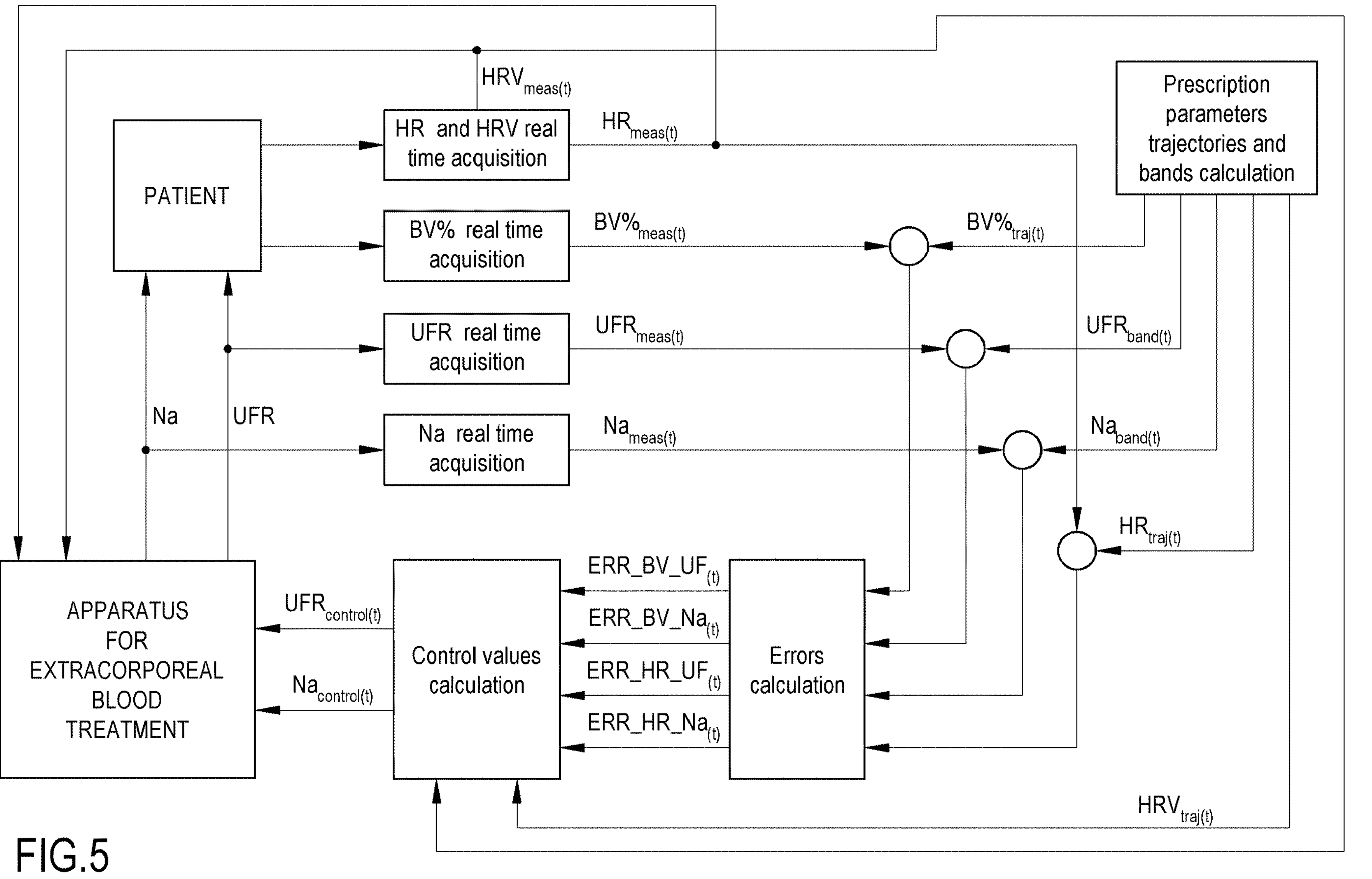
FIG. 5 is a block diagram relating to a third embodiment of the control procedure of the invention.

$3^{rd}$ Embodiment—FIGS. 5 and 5A

According to a third embodiment, the fourth parameters are two: heart rate (HR) and variation of heart rate (HRV) and the procedure is a combination of the $1^{st}$ embodiment and of the $2^{nd}$ embodiment. Indeed, as shown in the flow diagram of FIG. 5A, the control unit CPU calculates first values of the second parameter control value ($UFR_{control(t)}$; $WLR_{control(t)}$; $WL_{control(t)}$) on the basis of two parameter errors (the first error parameter ($ERR\_BV\ \%\_UF_{(t)}$) correlated to the variation of blood volume (BV %), the first error parameter ($ERR\_BV\ \%\_UF_{(t)}$) correlated to the heart rate HR)) and of the actual value of the second parameter ($UFR_{meas(t-\Delta t)}$; $WLR_{meas(t-\Delta t)}$; $WL_{meas(t-\Delta t)}$) relating to a preceding control instant. The control unit CPU also calculates first values of the third parameter control value ($Cd_{control(t)}$; $Na_{control(t)}$) on the basis of two parameter errors (the second error parameter ($ERR\_BV\ \%\_Na_{(t)}$) correlated to the variation of blood volume (BV %), the second error parameter ($ERR\_HR\_Na_{(t)}$) correlated to the heart rate (HR)) and of the actual value of the third parameter ($Cd_{meas(t-\Delta t)}$, $Na_{meas(t-\Delta t)}$) relating to a preceding control instant. Once that the first values of the second parameter control value ($UFR_{control(t)}$; $WLR_{control(t)}$; $WL_{control(t)}$) and of the third parameter control value ($Cd_{control(t)}$; $Na_{control(t)}$) have been calculated on the basis of the four parameter errors, these first values may be corrected as a function of a comparison between the actual value of the variation of heart rate ($HRV_{meas(t)}$) with the prescription value of the variation of heart rate ($HRV_{traj(t)}$).

For instance, as in the $1^{st}$ embodiment, the second parameter control value ($UFR_{control(t)}$; $WLR_{control(t)}$; $WL_{control(t)}$) and/or the third parameter control value ($Cd_{control(t)}$; $Na_{control(t)}$) are decreased with respect to their respective calculated first values in order to limit the variation of heart rate ($HRV_{meas(t)}$) and to keep it below the fourth parameter threshold.

In other embodiments, the control unit CPU may be configured to take into account also at least a fifth parameter, like the infusion flow rate ($Q_{INF}$) and/or the transmembrane pressure (TMP), to calculate a fifth parameter control value and to impose also a fifth parameter control value during the time interval consecutive to the instant in which the control is made such that: the actual values of the variation of blood volume ($BV\ \%_{meas(t)}$) track the prescription values of the variation of blood volume ($BV\ \%_{traj(t)}$) over the predetermined treatment time and the actual values of the heart rate ($HR_{meas(t)}$) or variation of heart rate ($HRV_{meas(t)}$) track the respective prescription values over the predetermined treatment time. The control procedure above described is automatically managed by the control unit CPU. In case, despite the automatic control procedure, the actual values of the variation of blood volume ($BV\ \%_{meas(t)}$) and/or the actual values of the heart rate ($HR_{meas(t)}$) and/or of variation of heart rate ($HRV_{meas(t)}$) move away from the respective prescription values (move away from a prescribed trajectory or move outside a prescribed band or move above or below a prescribed threshold), the control unit CPU is programmed to issue an alarm signal to alert the staff and/or to stop the blood treatment.

While the invention has been described in connection with what is presently considered to be the most practical and preferred embodiment, it is to be understood that the invention is not to be limited to the disclosed embodiment, but on the contrary, is intended to cover various modifications and equivalent arrangements, all included within the scope of the appended claims.

The invention claimed is:

1. An apparatus for extracorporeal blood treatment, comprising:
   - a treatment unit having a first chamber and a second chamber separated from one another by a semipermeable membrane;
   - a blood removal line connected to an inlet port of the first chamber and configured to remove blood from a patient connected to the blood removal line,
   - a blood return line connected to an outlet port of the first chamber and configured to return treated blood to the patient connected to the blood removal line; the blood removal line, the blood return line, and the first chamber being part of an extracorporeal blood circuit;
   - at least one fluid evacuation line connected to an outlet port of the second chamber;
   - a supply line connected to one or both of an inlet port of the second chamber and the extracorporeal blood circuit;
   - a plurality of sensor devices configured to detect actual values of a plurality of parameters of the extracorporeal blood treatment;
   - a control unit connected to the plurality of sensor devices and configured to receive prescription values of said plurality of parameters to be reached in the patient or to follow over a predetermined treatment time and to obtain, through the plurality of sensor devices, the actual values of said plurality of parameters during the extracorporeal blood treatment; wherein said plurality of parameters comprise:
   - a first parameter being a variation in blood volume of the patient;
   - a second parameter being one of an ultrafiltration flow rate through the semipermeable membrane, a weight loss rate of the patient, and an accumulated weight loss;
   - a third parameter being a conductivity of a liquid crossing the supply line or a concentration of a substance in a liquid crossing the supply line;
   - a fourth parameter being one or both of a heart rate of the patient and a variation of heart rate of the patient;

wherein the control unit is configured to perform, at temporally consecutive control instants, a control procedure comprising:
   - calculating, on the basis of the actual values and the prescription values, the following control values to be set during a time interval after each control instant in which the control is made:
     - a second parameter control value; and
     - a third parameter control value;
   - imposing at least one of the second parameter control value and the third parameter control value during a time interval consecutive to the control instant in which the control is made such that:
     - the actual values of the first parameter track the prescription values of the first parameter over the predetermined treatment time; and
     - the actual values of the fourth parameter track the prescription values of the fourth parameter over the predetermined treatment time,
   - wherein first values of one or both of the second parameter control value and the third parameter control value are calculated on the basis of the actual values and of the prescription values of the first parameter, second parameter, and third parameter and then said first values are corrected on the basis of the actual values and of the prescription values of the fourth parameter.

2. The apparatus of claim 1, wherein the heart rate or the variation of heart rate is acquired in real time.

3. The apparatus of claim 2, wherein the prescription values of the fourth parameter define a fourth parameter trajectory and wherein tracking the prescription values of the fourth parameter comprises: keeping or moving the actual values of the fourth parameter on said fourth parameter trajectory or in a neighbourhood of said fourth parameter trajectory.

4. The apparatus of claim 3, wherein the fourth parameter trajectory comprises a succession of points defining a line over treatment time; wherein the fourth parameter trajectory is constant or time-varying.

5. The apparatus of claim 3, wherein, the fourth parameter is the heart rate and receiving or setting the prescription values of the fourth parameter comprises:
   - setting a target heart rate to be reached at the end of the blood treatment, wherein the target heart rate is a heart rate target band;
   - measuring an initial heart rate of the patient;
   - calculating the fourth parameter trajectory taking into account the initial heart rate and the target heart rate.

6. The apparatus of claim 2, wherein the prescription values of the fourth parameter are defined by a fourth parameter band and wherein tracking the prescription values of the fourth parameter comprises: keeping or moving the actual values of the fourth parameter within said fourth parameter band.

7. The apparatus of claim 6, wherein the fourth parameter is the heart rate and the prescription values of the fourth parameter are the fourth parameter trajectory;
   - wherein calculating the second parameter control value comprises:
     - receiving the fourth parameter trajectory and the prescription values of the second parameter, wherein the prescription values of the second parameter are a second parameter band;
     - determining at least a first error parameter correlated to the fourth parameter on the basis of:
       - a difference between the actual value of the fourth parameter at the control instant and a corresponding value on the fourth parameter trajectory; and
       - a difference between an actual value of the second parameter at the control instant and at least a corresponding value of the second parameter band;
     - calculating the second parameter control value on the basis of the first error parameter, correlated to the fourth parameter, and of the actual value of the second parameter relating to a preceding control instant.

8. The apparatus of claim 6, wherein the fourth parameter is the heart rate and the prescription values of the fourth parameter are the fourth parameter trajectory;
   - wherein calculating the third parameter control value comprises:
     - receiving the fourth parameter trajectory and the prescription values of the third parameter,
     - wherein the prescription values of the third parameter are a third parameter band;
     - determining at least a second error parameter correlated to the fourth parameter on the basis of:

a difference between the actual value of the fourth parameter at the control instant and a corresponding value on the fourth parameter trajectory, and a difference between an actual value of the third parameter at the control instant and at least a corresponding value of the third parameter band, and calculating the third parameter control value on the basis of the second error parameter, correlated to the fourth parameter, and of the actual value of the third parameter relating to a preceding control instant.

9. The apparatus of claim 6, wherein a fourth parameter trajectory is a mid line of the fourth parameter band, wherein the mid line of the fourth parameter band is in the middle and equally spaced from an upper trajectory and a lower trajectory, or is eccentric compared to the upper trajectory and the lower trajectory.

10. The apparatus of claim 6, wherein the fourth parameter band comprises a plurality of points delimited between an upper trajectory and a lower trajectory over treatment time; wherein the upper trajectory and the lower trajectory are constant or time-varying.

11. The apparatus of claim 2, wherein the prescription values of the fourth parameter define a fourth parameter threshold and wherein tracking the prescription values of the fourth parameter comprises: keeping or moving the actual values of the fourth parameter below or above said fourth parameter threshold.

12. The apparatus of claim 11, wherein calculating the second parameter control value comprises:

comparing the actual value of the fourth parameter with the prescription value of the fourth parameter at the control instant in which the control is made;

calculating the second parameter control value to be imposed during the time interval consecutive to the control instant as a function of said comparison.

13. The apparatus of claim 12, wherein the fourth parameter is the variation of heart rate and the prescription value of the fourth parameter is the fourth parameter threshold; wherein, if the actual value of the variation of heart rate is above the fourth parameter threshold or if a plurality of consecutive actual values of heart rate are above the fourth parameter threshold, the second parameter control value, to be imposed during the time interval consecutive to the control instant in which the control is made, is decreased with respect to the actual value of the second parameter at the control instant in which the control is made.

14. The apparatus of claim 11, wherein calculating the third parameter control value comprises:

comparing the actual value of the fourth parameter with the prescription value of the fourth parameter at the control instant in which the control is made;

calculating the third parameter control value to be imposed during the time interval consecutive to the control instant as a function of said comparison.

15. The apparatus of claim 14, wherein the fourth parameter is the variation of heart rate and the prescription value of the fourth parameter is the fourth parameter threshold; wherein, if the actual value of the variation of heart rate is above the fourth parameter threshold or if a plurality of consecutive actual values of heart rate are above the fourth parameter threshold, the third parameter control value, to be imposed during the time interval consecutive to the control instant in which the control is made, is decreased with respect to the actual value of the third parameter at the control instant in which the control is made.

16. The apparatus of claim 11, wherein the fourth parameter threshold comprises a succession of points defining a line over treatment time; wherein the fourth parameter threshold is constant or time-varying.

17. The apparatus of claim 1, wherein the plurality of sensor devices comprise:

a first sensor active on the extracorporeal blood circuit and configured to detect the actual values of the first parameter;

a second sensor active at least on the fluid evacuation line and configured to detect the actual values of the second parameter;

a third sensor active on the supply line and configured to detect the actual values of the third parameter;

a fourth sensor active on the patient or on the extracorporeal blood circuit and configured to detect the actual values of the fourth parameter.

18. The apparatus of claim 17, wherein the fourth sensor is selected from the group comprising: a patch, a wristband or an armband, a chest strap, a wearable electrode based ECG, a touch device, a breathable heart rate monitor, a contactless sensor, an ingestible pill, and an optical or pressure/force sensor placed on the extracorporeal blood circuit.

19. The apparatus of claim 1, comprising:

a first regulating device configured to regulate the second parameter, the first regulating device being connected to the control unit and being active on at least one of the extracorporeal blood circuit and the fluid evacuation line, a second regulating device configured to regulate a composition of the dialysis liquid, the second regulating device being connected to the control unit and being active on the supply line for regulating the third parameter;

and wherein the step of imposing the control values during the procedure comprises:

commanding the first regulating device to impose the second parameter control value;

commanding the second regulating device to impose third parameter control value.

20. The apparatus of claim 1, wherein, first, only the third parameter control value is imposed to track the prescription values of one or both of the first parameter and the fourth parameter and, then, the second parameter control value is also imposed if the prescription values of the one or both of the first parameter and the fourth parameter is/are not tracked correctly.

21. The apparatus of claim 1, wherein the prescription values of the first parameter define a first parameter trajectory and wherein tracking the prescription values of the first parameter comprises: keeping or moving the actual values of the first parameter on said first parameter trajectory or in a neighbourhood of said first parameter trajectory.

22. The apparatus of claim 21, wherein receiving the prescription values of the first parameter comprises:

estimating or measuring one or both of an initial concentration of haemoglobin and an initial blood volume;

setting a target variation in blood volume to be reached at the end of the blood treatment;

setting a blood treatment time;

calculating the first parameter trajectory taking into account one or both of the initial concentration of the haemoglobin and the initial blood volume, the target variation in blood volume, and the blood treatment time.

23. The apparatus of claim 1, wherein the fourth parameter is the heart rate and the actual value of the heart rate is an average of heart rate over a time interval.

24. The apparatus of claim 1, wherein the fourth parameter is variation of heart rate, wherein the variation of heart rate is calculated in real time from a heart signal and the actual value of variation of heart rate is calculated at each heartbeat or is an average over a plurality of heartbeats.

25. The apparatus of the preceding claim 24, wherein the variation of heart rate is calculated through at least one of: time domain methods, geometric methods, frequency-domain methods, and non-linear methods.

26. The apparatus of claim 1, wherein the fourth parameter comprises both the heart rate and the variation of heart rate; wherein first values of one or both of the second parameter control value and the third parameter control value are calculated on the basis of the actual values and of the prescription values of the first parameter, second parameter, third parameter, and heart rate and, then, said first values are corrected, limited, or corrected and limited on the basis of the actual values and of the prescription values of the variation of heart rate.

27. An apparatus for extracorporeal blood treatment, comprising:

- a treatment unit having a first chamber and a second chamber separated from one another by a semipermeable membrane;
- a blood removal line connected to an inlet port of the first chamber and configured to remove blood from a patient connected to the blood removal line,
- a blood return line connected to an outlet port of the first chamber and configured to return treated blood to the patient connected to the blood removal line: the blood removal line, the blood return line, and the first chamber being part of an extracorporeal blood circuit;
- at least one fluid evacuation line connected to an outlet port of the second chamber;
- a supply line connected to one or both of an inlet port of the second chamber and the extracorporeal blood circuit;
- a plurality of sensor devices configured to detect actual values of a plurality of parameters of the extracorporeal blood treatment;
- control unit connected to the plurality of sensor devices and configured to receive prescription values of said plurality of parameters to be reached in the patient or to follow over a predetermined treatment time and to obtain, through the plurality of sensor devices, the actual values of said plurality of parameters during the extracorporeal blood treatment; wherein said plurality of parameters comprise:
- a first parameter being a variation in blood volume of the patient;
- a second parameter being one of an ultrafiltration flow rate through the semipermeable membrane, a weight loss rate of the patient, and an accumulated weight loss;
- a third parameter being a conductivity of a liquid crossing the supply line or a concentration of a substance in a liquid crossing the supply line;
- a fourth parameter being one or both of a heart rate of the patient and a variation of heart rate of the patient:

wherein the control unit is configured to perform, at temporally consecutive control instants, a control procedure comprising:

- calculating, on the basis of the actual values and the prescription values the following control values to be set during a time interval after each control instant in which the control is made:
  - a second parameter control value; and
  - a third parameter control value;
- imposing at least one of the second parameter control value and the third parameter control value during a time interval consecutive to the control instant in which the control is made such that:
  - the actual values of the first parameter track the prescription values of the first parameter over the predetermined treatment time; and the actual values of the fourth parameter track the prescription values of the fourth parameter over the predetermined treatment time,

- wherein the fourth parameter comprises both heart rate and variation of heart rate; wherein first values of one or both of the second parameter control value and the third parameter control value are calculated on the basis of the actual values and of the prescription values of the first parameter, second parameter, third parameter, and the heart rate and, then, said first values are corrected, limited, or corrected and limited on the basis of the actual values and of the prescription values of the variation of heart rate.

28. An apparatus for extracorporeal blood treatment, comprising:

- a treatment unit having a first chamber and a second chamber separated from one another by a semipermeable membrane;
- a blood removal line connected to an inlet port of the first chamber and configured to remove blood from a patient connected to the blood removal line,
- a blood return line connected to an outlet port of the first chamber and configured to return treated blood to the patient connected to the blood removal line; the blood removal line, the blood return line, and the first chamber being part of an extracorporeal blood circuit;
- at least one fluid evacuation line connected to an outlet port of the second chamber;
- a supply line connected to one or both of an inlet port of the second chamber and the extracorporeal blood circuit;
- a plurality of sensor devices configured to detect actual values of a plurality of parameters of the extracorporeal blood treatment;
- a control unit connected to the plurality of sensor devices and configured to receive prescription values of said plurality of parameters to be reached in the patient or to follow over a predetermined treatment time and to obtain, through the plurality of sensor devices, the actual values of said plurality of parameters during the extracorporeal blood treatment; wherein said plurality of parameters comprise:
- a first parameter being a variation in blood volume of the patient;
- a second parameter being one of an ultrafiltration flow rate through the semipermeable membrane, a weight loss rate of the patient, and an accumulated weight loss;
- a third parameter being a conductivity of a liquid crossing the supply line or a concentration of a substance in a liquid crossing the supply line;
- a fourth parameter being one or both of a heart rate of the patient and a variation of heart rate of the patient;

wherein the control unit is configured to perform, at temporally consecutive control instants, a control procedure comprising:

calculating, on the basis of the actual values and the prescription values, the following control values to be set during a time interval after each control instant in which the control is made:

a second parameter control value; and a third parameter control value;

imposing at least one of the second parameter control value and the third parameter control value during a time interval consecutive to the control instant in which the control is made such that:

the actual values of the first parameter track the prescription values of the first parameter over the predetermined treatment time; and the actual values of the fourth parameter track the prescription values of the fourth parameter over the predetermined treatment time, wherein the heart rate or the variation of heart rate is acquired in real time, wherein the prescription values of the fourth parameter are defined by a fourth parameter band and wherein tracking the prescription values of the fourth parameter comprises: keeping or moving the actual values of the fourth parameter within said fourth parameter band, wherein the fourth parameter is the heart rate and the prescription values of the fourth parameter are the fourth parameter trajectory; wherein calculating the second parameter control value comprises:

receiving the fourth parameter trajectory and the prescription values of the second parameter, wherein the prescription values of the second parameter are a second parameter band;

determining at least a first error parameter correlated to the fourth parameter on the basis of:

a difference between the actual value of the fourth parameter at the control instant and a corresponding value on the fourth parameter trajectory; and a difference between an actual value of the second parameter at the control instant and at least a corresponding value of the second parameter band;

calculating the second parameter control value on the basis of the first error parameter, correlated to the fourth parameter, and of the actual value of the second parameter relating to a preceding control instant.

29. An apparatus for extracorporeal blood treatment, comprising:

a treatment unit having a first chamber and a second chamber separated from one another by a semipermeable membrane;

a blood removal line connected to an inlet port of the first chamber and configured to remove blood from a patient connected to the blood removal line, a blood return line connected to an outlet port of the first chamber and configured to return treated blood to the patient connected to the blood removal line; the blood removal line, the blood return line, and the first chamber being part of an extracorporeal blood circuit;

at least one fluid evacuation line connected to an outlet port of the second chamber;

a supply line connected to one or both of an inlet port of the second chamber and the extracorporeal blood circuit;

a plurality of sensor devices configured to detect actual values of a plurality of parameters of the extracorporeal blood treatment;

a control unit connected to the plurality of sensor devices and configured to receive prescription values of said plurality of parameters to be reached in the patient or to follow over a predetermined treatment time and to obtain, through the plurality of sensor devices, the actual values of said plurality of parameters during the extracorporeal blood treatment; wherein said plurality of parameters comprise:

a first parameter being a variation in blood volume of the patient;

a second parameter being one of an ultrafiltration flow rate through the semipermeable membrane, a weight loss rate of the patient, and an accumulated weight loss;

a third parameter being a conductivity of a liquid crossing the supply line or a concentration of a substance in a liquid crossing the supply line;

a fourth parameter being one or both of a heart rate of the patient and a variation of heart rate of the patient;

wherein the control unit is configured to perform, at temporally consecutive control instants, a control procedure comprising:

calculating, on the basis of the actual values and the prescription values, the following control values to be set during a time interval after each control instant in which the control is made:

a second parameter control value; and a third parameter control value;

imposing at least one of the second parameter control value and the third parameter control value during a time interval consecutive to the control instant in which the control is made such that:

the actual values of the first parameter track the prescription values of the first parameter over the predetermined treatment time; and the actual values of the fourth parameter track the prescription values of the fourth parameter over the predetermined treatment time, wherein the heart rate or the variation of heart rate is acquired in real time, wherein the prescription values of the fourth parameter are defined by a fourth parameter band and wherein tracking the prescription values of the fourth parameter comprises: keeping or moving the actual values of the fourth parameter within said fourth parameter band, wherein the fourth parameter is the heart rate and the prescription values of the fourth parameter are the fourth parameter trajectory; wherein calculating the third parameter control value comprises:

receiving the fourth parameter trajectory and the prescription values of the third parameter, wherein the prescription values of the third parameter are a third parameter band;

determining at least a second error parameter correlated to the fourth parameter on the basis of:

a difference between the actual value of the fourth parameter at the control instant and a corresponding value on the fourth parameter trajectory, and a difference between an actual value of the third parameter at the control instant and at least a corresponding value of the third parameter band, and calculating the third parameter control value on the basis of the second error parameter, correlated to the fourth parameter, and of the actual value of the third parameter relating to a preceding control instant.

30. An apparatus for extracorporeal blood treatment, comprising:

a treatment unit having a first chamber and a second chamber separated from one another by a semipermeable membrane;

a blood removal line connected to an inlet port of the first chamber and configured to remove blood from a patient connected to the blood removal line, a blood return line connected to an outlet port of the first chamber and configured to return treated blood to the patient connected to the blood removal line; the blood removal line, the blood return line, and the first chamber being part of an extracorporeal blood circuit;

at least one fluid evacuation line connected to an outlet port of the second chamber;

a supply line connected to one or both of an inlet port of the second chamber and the extracorporeal blood circuit;

a plurality of sensor devices configured to detect actual values of a plurality of parameters of the extracorporeal blood treatment;

a control unit connected to the plurality of sensor devices and configured to receive prescription values of said plurality of parameters to be reached in the patient or to follow over a predetermined treatment time and to obtain, through the plurality of sensor devices, the actual values of said plurality of parameters during the extracorporeal blood treatment; wherein said plurality of parameters comprise:

a first parameter being a variation in blood volume of the patient;

a second parameter being one of an ultrafiltration flow rate through the semipermeable membrane, a weight loss rate of the patient, and an accumulated weight loss;

a third parameter being a conductivity of a liquid crossing the supply line or a concentration of a substance in a liquid crossing the supply line;

a fourth parameter being one or both of a heart rate of the patient and a variation of heart rate of the patient;

wherein the control unit is configured to perform, at temporally consecutive control instants, a control procedure comprising:

calculating, on the basis of the actual values and the prescription values, the following control values to be set during a time interval after each control instant in which the control is made:

a second parameter control value; and a third parameter control value;

imposing at least one of the second parameter control value and the third parameter control value during a time interval consecutive to the control instant in which the control is made such that:

the actual values of the first parameter track the prescription values of the first parameter over the predetermined treatment time; and the actual values of the fourth parameter track the prescription values of the fourth parameter over the predetermined treatment time, wherein, first, only the third parameter control value is imposed to track the prescription values of one or both of the first parameter and the fourth parameter and, then, the second parameter control value is also imposed if the prescription values of the one or both of the first parameter and the fourth parameter is/are not tracked correctly.

* * * * *